United States Patent
Hogan et al.

(10) Patent No.: US 11,618,917 B2
(45) Date of Patent: Apr. 4, 2023

(54) METHODS FOR MICROBIAL DNA ANALYSIS

(71) Applicants: Michael Edward Hogan, Tucson, AZ (US); Benjamin Alan Katchman, Tucson, AZ (US); Candy Mavis Rivas, Tucson, AZ (US); Yasmine Eve Baca, San Tan Valley, AZ (US)

(72) Inventors: Michael Edward Hogan, Tucson, AZ (US); Benjamin Alan Katchman, Tucson, AZ (US); Candy Mavis Rivas, Tucson, AZ (US); Yasmine Eve Baca, San Tan Valley, AZ (US)

(73) Assignee: PathogenDx, Inc., Scottsdale, AZ (US)

(*) Notice: Subject to any disclaimer, the term of this patent is extended or adjusted under 35 U.S.C. 154(b) by 0 days.

(21) Appl. No.: 17/735,041

(22) Filed: May 2, 2022

(65) Prior Publication Data

US 2022/0267832 A1 Aug. 25, 2022

Related U.S. Application Data

(63) Continuation-in-part of application No. 16/816,481, filed on Mar. 12, 2020, now Pat. No. 11,319,582.

(60) Provisional application No. 62/876,054, filed on Jul. 19, 2019.

(51) Int. Cl.
*C12Q 1/6806* (2018.01)
*C12Q 1/6851* (2018.01)

(52) U.S. Cl.
CPC ......... *C12Q 1/6806* (2013.01); *C12Q 1/6851* (2013.01); *C12Y 301/31001* (2013.01)

(58) Field of Classification Search
CPC .................................................. C12Q 1/6806
See application file for complete search history.

(56) References Cited

U.S. PATENT DOCUMENTS

| | | | | |
|---|---|---|---|---|
| 2001/0047966 A1* | 12/2001 | Colpan | .............. | C12N 15/1017 210/808 |
| 2002/0172972 A1* | 11/2002 | Tabor | .................. | C12Q 1/6848 435/6.12 |
| 2009/0042255 A1* | 2/2009 | Liu | ..................... | C12N 15/1003 435/91.1 |
| 2021/0008552 A1* | 1/2021 | Regan | ................ | G01N 35/1095 |

OTHER PUBLICATIONS

Grabuschnig, S. et al., Putative Origins of Cell-Free DNA in Humans: A Review of Active and Passive Nucleic Acid Release Mechanisms, Int. J. Mol. Sci., vol. 21, 8062, pp. 1-24 (Year: 2020).*
Villareal, J.V. et al., DNase I and Proteinase K eliminate DNA from injured or dead bacteria but not from living bacteria in microbial reference systems and natural drinking water biofilms for subsequent molecular biology analyses, J. Microbiol. Meth., vol. 94, pp. 161-169 (Year: 2013).*
Mukhopadhyay, U.K. et al., A low-cost, rapid, sensitive and reliable PCR-based alternative method for predicting the presence of possible live microbial contaminants in food, Current Science, vol. 83, pp. 53-56 (Year: 2002).*
Nadugala, L.M.N.S. et al., The effect of DNaseI enzyme on food pathogens subjected to different food processing treatmentJ. Natn. Sci. Foundation Sri Lanka, vol. 35, pp. 167-173 (Year: 2007).*
Do, H.T.T. et al., DNase I treated DNA-PCR based detection of food pathogens immobilized by metal hydroxides, World J. Microbiol. Technol., vol. 25, pp. 1491-1495 (Year: 2009).*

* cited by examiner

*Primary Examiner* — Teresa E Strzelecka
(74) *Attorney, Agent, or Firm* — Benjamin Aaron Adler

(57) ABSTRACT

Provided herein are methods for isolating nucleic acids from intact cells in a sample of intact cells and cell free nucleic acids. The intact cells and cell free nucleic acids are captured and concentrated within the pores of a silicate matrix in a microporous silicate filter. Within the silicate matrix the cell free nucleic acids are degraded with a nuclease, the intact cells are lysed with the released DNA binding to the silicate, the nuclease treated cell free nucleic acids and contaminants from the lysed are washed from the silicate matrix and the DNA bound to the silicate is eluted therefrom to form an isolated DNA product.

12 Claims, 9 Drawing Sheets

Specification includes a Sequence Listing.

✖ Nuclease Treated Cell Free DNA, RNA

METHODS FOR MICROBIAL DNA ANALYSIS

CROSS-REFERENCE TO RELATED APPLICATIONS

This continuation-in-part application claims benefit of priority under 35 U.S.C. § 120 of pending non-provisional application U.S. Ser. No. 16/816,481, filed Mar. 12, 2020, which claims benefit of priority under 35 U.S.C. § 119(e) of provisional application U.S. Ser. No. 62/876,054, filed Jul. 19, 2019, the entirety of both of which is hereby incorporated by reference.

BACKGROUND OF THE INVENTION

Field of the Invention

The present invention relates to the technical field of DNA based cell analysis. More specifically, the present invention relates to methods of isolating intact cells from contaminating dead cells, biofilm and cellular debris and to methods of isolating cellular nucleic acids from cell free nucleic acids via a macroporous filter.

Description of the Related Art

Filtration and centrifugation are useful methods to collect microbes for subsequent DNA analysis. When suspended as aerosol particulates, microbes such as bacteria or fungi may be collected by passage through a filter with a pore size less than about 0.5 µm, because the longest dimension of such microbes is generally larger than the 0.5 µm cut off of such membranes. Similarly, microbes in water may also be collected by filtration, or by centrifugation at 1,000×g-15,000× g, because suspended microbial particles are denser that water and with a dimension >0.5 µm are large enough to be sedimented to the bottom of a centrifuge tube, to form a pellet of microbial cells.

Although filter-based and centrifugation-based microbial collection and purification is known to be useful for DNA analysis in the context of agricultural, food and environmental screening, in the particular case of microbial contamination on surfaces—especially plant surfaces, animal skin, mechanical devices and processing surfaces—the occurrence of a biofilm (1) may complicate the collection of microbes by these methods, particularly when the objective is DNA analysis from the collected material. Briefly, when growing on surfaces, microbes, especially bacteria and fungi, have evolved to create a thick, physically durable hydrogel "biofilm" which surrounds them on a surface, to enable stable microbial attachment and growth on the underlying plant, skin, mechanical device or processing surface (2-4).

When microbes are dispersed off of a surface into the air or a liquid, they may be accompanied by patches of the biofilm. Whether still attached together or not, microbes and biofilm will in most cases be captured by filters or sedimented by centrifugation in a way that is indistinguishable from capture of the pure microbes alone. As a result, microbial DNA derived from the biofilm, comprising the DNA from live plus dead microbes, becomes indistinguishable from microbial DNA of the captured live microbes. This leads to erroneous assessment of live microbes using microbial DNA analysis.

Current methods for distinguishing live and dead cells in a mixture use the property of intact cells, but not dead cells, to exclude DNA-reactive dyes, such as propidium azide from their cytoplasm. For example the dye propidium azide (5-7), will not penetrate intact cells, thereby selectively inactivating the DNA in the dead cell population. The DNA-propidium azide conjugates formed from dead cells are unresponsive to PCR and other types of DNA based analysis (8) whereby amplicons formed by PCR correspond only to the DNA in intact cells, however, dyes like propidium azide interfere with PCR assays. As a result, a time-consuming purification step is required to remove unreacted propidium azide from the sample that would also result is significant loss of the microbial DNA of interest.

Silicates especially silicon oxide ($SiO_2$) containing glasses or other silicate composites such as borosilicate glass may be made into macroporous filters, where macroporous is defined by an effective pore size >>1 µm. Such silicate based filters may be made from packed, woven or matted fiberglass or from packed diatomaceous earth or from sintered glass frit or from packed silicate microspheres. In all cases, at or near physiological pH and ionic strength, the silicate surfaces presented by such macroporous matrices are generally inert with respect to interaction with cells or protein, DNA or RNA or other biomolecules. At physiological ionic strength and pH, however, such macroporous silicate matrices, if they are presented as a barrier layer thicker than about 1 mm, provide a significant obstruction to the flow of particles in the about 1 µm to about 20 µm size range when they are presented as a suspension in water solution due to tortuosity.

Thus, the prior art is deficient in methods of nucleic acid analysis that distinguishes dead or cell free microbial DNA from live microbial DNA in intact cells. Particularly, there is a need in the art for methods that utilize silicate macroporous filters to isolate DNA from intact microbes captured and concentrated inside the silicate filters. The present invention fulfills this long-standing need and desire in the art.

SUMMARY OF THE INVENTION

The present invention is directed to a method for isolating nucleic acids from intact cells. In the method a sample comprising intact cells and cell free nucleic acids is obtained. The intact cells and the cell free nucleic acids are captured within a matrix comprising a macroporous filter. The captured cell free nucleic acids are degraded in situ with a nuclease. Cellular nucleic acids are released from the captured intact cells and eluted from the matrix with an elution buffer to produce an isolated nucleic acid product.

The present invention also is directed to a related method for isolating nucleic acids from intact cells. In the method a sample comprising intact cells and cell free nucleic acids is obtained and the sample is suspended in a suspension buffer to form a cellular suspension. The cellular suspension is flowed directionally through a macroporous filter comprising a silicate matrix to capture the intact cells and cell free nucleic acids within pores in the silicate matrix. The cell free nucleic acids are degraded in situ within the silicate matrix with a nuclease. A lysing/binding buffer is added to the macroporous filter to lyse the captured intact cells to release cellular nucleic acids therefrom, where the cellular nucleic acids bind to the silicate matrix. An elution buffer is added to the silicate matrix to elute the cellular nucleic acids from the macroporous filter to produce an isolated nucleic acid product.

The present invention is directed further to a method for producing a DNA product from a microbial sample. In the method obtaining the microbial sample comprising intact cells and cell free DNA is obtained and suspended in a suspension buffer to form a microbial suspension of the intact cells and cell free DNA. The intact cells and cell free DNA comprising the microbial suspension are entrapped within silicate matrix pores of a microporous silicate filter upon application thereto. A micrococcal nuclease is added to the microporous silicate filter to degrade the cell free DNA entrapped therewithin. Microbial DNA is released from the intact cells entrapped within the silicate matrix pores and the same binds to the microporous silicate in the filter. The microbial DNA is eluted from the microporous silicate with an elution buffer to release the same, thereby producing the DNA product. The present invention is directed to a related method further comprising analyzing the DNA product to quantify the DNA or identify the intact cell or a combination thereof.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 2A shows mean Ct data from qPCR analysis from live and heat-killed *E. coli* pellets incubated with or without DNAse I (an endonuclease which produces single strand breaks in DNA). FIG. 2B shows mean Ct from qPCR performed using a no template control (NTC) and from live and heat-killed *E. coli* supernatants obtained after centrifuging a *E. coli* cell suspension to obtain the pellets described in FIG. 2A.

FIG. 5A shows microarray results for dead *E. coli*. FIG. 5B shows microarray results for *Salmonella enterica* (*S. enterica*).

FIG. 6A is a representative qPCR analysis in *A. niger* samples processed without ("MN buffer alone") or with ("MN") micrococcal nuclease. FIG. 6B is a representative qPCR analysis in *E. coli* samples processed without or with micrococcal nuclease. FIG. 6C is a representative qPCR analysis in *S. enterica* samples processed without or with micrococcal nuclease.

FIG. 7A shows the microarray results for *E. coli*. FIG. 7B shows the microarray results for *S. enterica*. FIG. 7C shows the microarray results for *Aspergillus niger* (*A. niger*).

FIG. 8A is a comparison of physical enrichment alone with physical enrichment combined with biochemical enrichment using micrococcal nuclease for *S. enterica*. FIG. 8B is a comparison of physical enrichment alone with physical enrichment combined with biochemical enrichment using micrococcal nuclease for *S. cerevisiae*.

FIG. 10A illustrates the macroporous silicate ($SiO_2$) filter in the flow chamber. FIG. 10B illustrates the application of the cells and cell free DNA to the macroporous silicate filter in physiological salt and pH. FIG. 10C illustrates capture and concentration of cells within the silicate filter by directional flow. FIG. 10D illustrates the in situ enzymatic degradation of the cell free DNA trapped inside the macroporous silicate filter. FIG. 10E illustrates the repeated flow mixing of a lysis/binding solution through the matrix in the silicate filter to induce cell lysis and to induce cellular DNA binding to the pore surfaces of the macroporous silicate filter matrix. FIG. 10F illustrates the repeated flow mixing through the matrix to wash and purify the liberated cellular DNA while it remains bound to the pore surfaces of the macroporous silicate matrix. FIG. 10G illustrates the repeated flow mixing through the matrix with an elution buffer to release the purified DNA from the macroporous silicate filter.

DETAILED DESCRIPTION OF THE INVENTION

Figure 1:
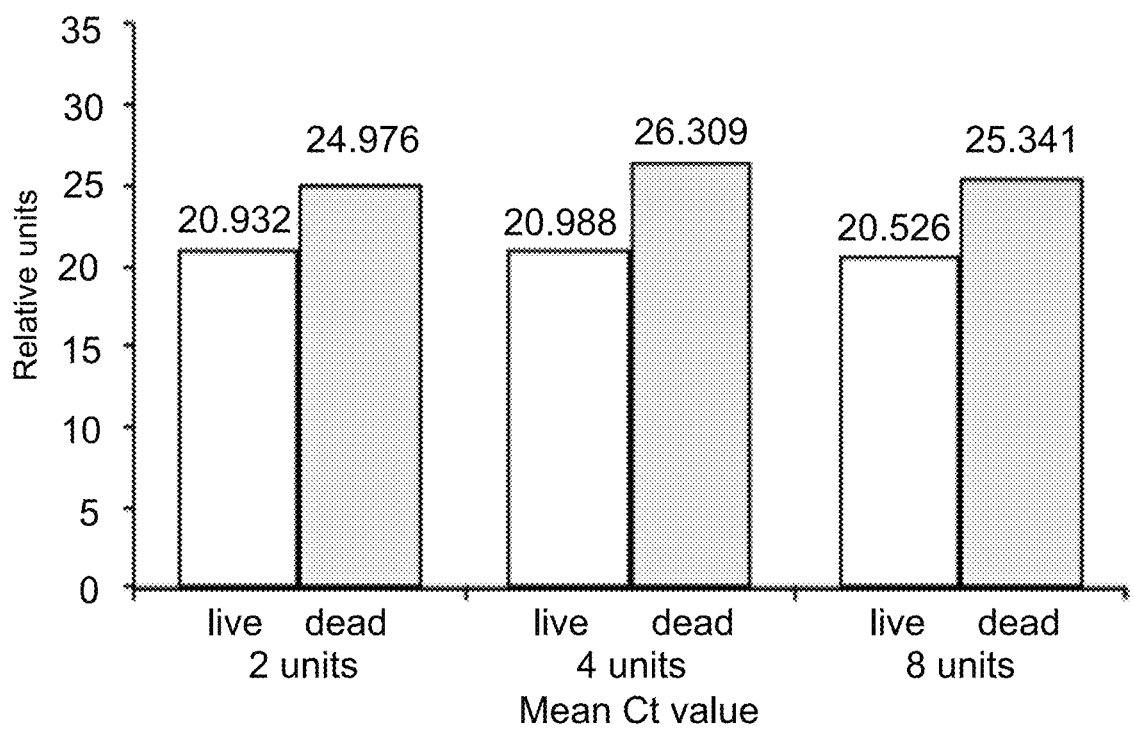
FIG. 1 shows a live cell (white) versus dead (gray) cell qPCR analysis for *Escherichia coli* (*E. coli*) DNA isolated using the claimed method.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, "intact cells" refers to live cells that are capable of growing and replicating.

As used herein, "double-stranded DNA specific deoxyribonuclease" refers to a deoxyribonuclease that generates more than 50% of double-stranded DNA specific cleavages.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure. For example, a relative centrifugal speed from 900 to 16,500×g is encompassed by about 1,000×g to about 15,000×g.

As used herein, "cell free nucleic acids" refers to nucleic acids, for example, DNAs and/or RNAs, in dead cells, contaminating dead cells, contaminating biofilm, or cell debris.

As used herein, "tortuosity" refers to a standard principle in polymer and parcel dynamics in the fluid phase. This describes that for fluids and polymers or particulates in such fluids, the paths for traversal of the pores of a solid matrix are generally not linear where the winding, irregular and branched nature of such paths restricts the flow of polymers and solids suspended in a fluid when the size of the polymer or suspended particulates are comparable to that of the effective pore size of the matrix through which they must pass. Thus, small molecules (<<0.1 nM) flow readily through a macroporous matrix with pores (>>1 μm). Larger polymer chains and suspected particles with a radius of gyration or a fixed solid dimension in that same macroporous size range (>21 μm) in a suspension display progressively more restricted flow through a surrounding macroporous phase.

As used herein, "barrier filter", refers to a macroporous matrix of dimensions relative to those of intact cells that enables the entrapment or capture of cells in an aqueous suspension within the matrix pores as the rate of flow of the aqueous suspension through the matrix is restricted.

As used herein, "Boom chemistry", refers to the adsorptive binding of DNA and RNA polymer chains in fluid contact with silicates at neutral to weakly acidic pHs upon addition of chaotropes, most particularly guanidinium HCl (GuHCl) or guanidinium thiocyanate (GuSCN) at >4N, alone or when augmented with an alcohol, such as ethanol at >25% by volume.

As used herein, "silicon dioxide", "SiO$_2$" and "silicate" are used interchangeably.

In one embodiment of the present invention there is provided a method for isolating nucleic acids from intact cells, comprising the steps of obtaining a sample comprising intact cells, contaminating dead cells, cell debris, and biofilm; performing a first separation on the sample to obtain a first fraction comprising the intact cells and the contaminating dead cells; suspending the first fraction in a buffered solution to obtain a suspension; performing a second separation on the suspension to obtain a second fraction comprising the intact cells; and isolating the nucleic acids from the intact cells in the second fraction.

In a further embodiment, prior to performing the first separation, the method further comprises the steps of capturing the intact cells, the contaminating dead cells, the cell debris, and the biofilm by filtration; and suspending the intact cells, the contaminating dead cells, the cell debris, and the biofilm in a buffered solution.

In yet another further embodiment the method comprises measuring the relative abundance of the intact cells in the sample, comprising the steps of determining a total cell count in the sample; amplifying, in at least one amplification, a target nucleotide sequence in the nucleic acids isolated from the intact cells using a pair of primers having a nucleotide sequence complementary to the target nucleotide sequence to generate a plurality of amplicons; quantitating the amplicons in the plurality; correlating the quantity of amplicons to a count of the intact cells in the sample; and comparing the count of the intact cells to the total cell count thereby determining the relative abundance of the intact cells in the sample. In this further embodiment the pair of primers may further comprise a fluorescent label, where the method generates a plurality of fluorescent labeled amplicons. In an aspect of this further embodiment the nucleic acid is an RNA and prior to the amplifying step, the method further comprises the step of performing a reverse transcription thereon.

In all these embodiments and aspects thereof, the steps of performing the first separation and the second separation independently may comprise centrifuging or filtering or a combination thereof. Also in all embodiments and aspects the step of isolating the nucleic acids may comprise the steps of disrupting the intact cells to release the nucleic acids; and isolating the nucleic acids therefrom. In addition the nucleic acid may be a DNA or an RNA. Furthermore, the intact cell may be a bacterial cell, a fungal cell, an algal cell, a protozoan cell, an animal cell, or a plant cell.

In another embodiment of the present invention there is provided a for isolating nucleic acids from intact cells, comprising the steps of obtaining a sample comprising intact cells, contaminating dead cells, cell debris, and biofilm; performing a first separation on the sample to obtain a first fraction comprising the intact cells and the contaminating dead cells; suspending the first fraction in a nuclease reaction buffer to obtain a suspension; incubating the suspension with a nuclease to degrade nucleic acids in the contaminating dead cells to obtain a partially nuclease-degraded sample; performing a second separation on the partially nuclease-degraded sample to obtain a second fraction comprising the intact cells; and isolating the nucleic acids from the intact cells in the second fraction.

In this embodiment further method steps may comprise those method steps performed prior to performing the first separation, those method steps for performing the first separation and the second separation and those method steps for isolating the nucleic acids and are as described supra. Also in this embodiment those method steps for measuring the relative abundance of the intact cells in the sample with or without fluorescent labeled pairs of primers and the amplicons so generated and the method step where the nucleic acid is RNA where prior to the measuring the relative abundance of intact cells, reverse transcription is performed thereon are as described supra. In addition the intact cell may be as described supra.

In all embodiments the nucleic acid may be a DNA or an RNA. Also the nuclease may be an endonuclease, an exonuclease or an endo-exonuclease. Particularly, the nuclease may be a single-stranded nucleic acid specific nuclease or a double-stranded nucleic acid specific nuclease. Representative examples of the nuclease are a deoxyribonuclease I, a deoxyribonuclease II, an exonuclease IV, an exonuclease V, an exonuclease VI, a ribonuclease A, a ribonuclease H, a ribonuclease III, a exoribonuclease I, a exoribonuclease II, or a micrococcal nuclease, or a combination thereof. A specific example of a nuclease is a micrococcal nuclease.

In yet another embodiment of the present invention there is provided a method for isolating DNA from intact cells, comprising the steps of obtaining a sample comprising intact cells and contaminating dead cells, cell debris and biofilm; performing a first separation on the sample to obtain a first fraction comprising the intact cells and the contaminating dead cells; suspending the first fraction in a deoxyribonuclease reaction buffer to obtain a suspension; incubating the suspension with a double stranded DNA specific deoxyribonuclease to degrade DNA in the contaminating dead cells to obtain a partially deoxyribonuclease-degraded sample; performing a second separation on the partially deoxyribonuclease-degraded sample to obtain a second fraction comprising the intact cells; and isolating the DNA from the intact cells in the second fraction. In this embodiment the deoxyribonuclease may be a micrococcal nuclease.

In this embodiment further method steps may comprise those method steps performed prior to performing the first separation, those method steps for performing the first separation and the second separation and those method steps for isolating the nucleic acids and are as described supra. Also in this embodiment those method steps for measuring the relative abundance of the intact cells in the sample with or without fluorescent labeled pairs of primers and the amplicons so generated are as described supra. In addition the intact cell may be as described supra.

In yet another embodiment of the present invention there is provided a method for isolating nucleic acids from intact cells, comprising the steps of obtaining a sample comprising intact cells and cell free nucleic acids; capturing the intact cells and the cell free nucleic acids within a matrix comprising a macroporous filter; degrading in situ the captured cell free nucleic acids with a nuclease; releasing cellular nucleic acids from the captured intact cells; and eluting the cellular nucleic acids from the matrix with an elution buffer to produce an isolated nucleic acid product.

In one aspect of this embodiment the capturing step may comprise suspending the intact cells and the cell free nucleic acids in a suspension buffer to form a cellular suspension; flowing directionally the cellular suspension through the macroporous filter; and entrapping the intact cells and the cell free nucleic acids within macroporous matrix pores to concentrate the same therewithin. In another aspect of this embodiment the releasing step may comprise flowing a lysis/binding solution at least once through the macroporous matrix to lyse the intact cells to release cellular nucleic acids, where the released cellular nucleic acids bind to the matrix; and flowing a washing solution at least once through the matrix to remove nuclease treated cell free nucleic acids and contaminants from lysed cells.

In this embodiment and both aspects thereof the macroporous filter may comprise a silicate matrix. Particularly, the silicate matrix may comprise a glass made of silicon oxide alone or in combination with boron oxide or aluminum oxide. Also, the nucleic acids may be DNA or RNA or a combination thereof. In addition the nuclease may be a micrococcal nuclease, deoxyribonuclease I, a deoxyribonuclease II, an exonuclease IV, an exonuclease V, an exonuclease VI, a ribonuclease A, a ribonuclease H, a ribonuclease III, a exoribonuclease I, or an exoribonuclease II, or a combination thereof. Particularly, the nuclease may be a micrococcal nuclease. Furthermore, the intact cells may be bacterial cells, fungal cells, animal cells, or plant cells. Further still the microbial sample may be obtained from plant tissue, human tissue or animal tissue, from a swab taken off a solid surface, from the air, or from a liquid.

In yet another embodiment of the present invention there is provided a method for isolating nucleic acids from intact cells, comprising the steps of obtaining a sample comprising intact cells and cell free nucleic acids; suspending the sample in a suspension buffer to form a cellular suspension; flowing directionally the cellular suspension through a macroporous filter comprising a silicate matrix to capture the intact cells and cell free nucleic acids within pores in the silicate matrix; degrading in situ within the silicate matrix the cell free nucleic acids with a nuclease; adding a lysing/binding buffer to the macroporous filter to lyse the captured intact cells to release cellular nucleic acids therefrom, said cellular nucleic acids binding to the silica matrix; and adding an elution buffer to the silicate matrix to elute the cellular nucleic acids from the macroporous filter to produce an isolated nucleic acid product.

In one aspect of this embodiment prior to adding an elution buffer the method may comprise flowing a washing solution at least once through the silica matrix to remove nuclease treated cell free nucleic acids and contaminants from lysed cells. In this embodiment and aspect thereof the nucleic acids may be DNA or RNA or a combination thereof. Also in this embodiment and aspect thereof the nuclease may be a micrococcal nuclease. In addition the intact cells may be bacterial cells, fungal cells, animal cells, or a plant cells. Furthermore, the microbial sample may be obtained from a swab taken from plant tissue, human tissue or animal tissue, from a swab taken off a solid surface, from the air, or from a liquid.

In yet another embodiment of the present invention there is provided a method for producing a DNA product from a microbial sample, comprising the steps of obtaining the microbial sample comprising intact cells and cell free DNA; suspending the microbial sample in a suspension buffer to form a microbial suspension of the intact cells and cell free DNA; entrapping the intact cells and cell free DNA comprising the microbial suspension within silicate matrix pores of a microporous silicate filter upon application thereto; adding a micrococcal nuclease to the microporous silicate filter to degrade the cell free DNA entrapped therewithin; releasing microbial DNA from the intact cells entrapped within the silicate matrix pores and binding the same to the microporous silicate in the filter; and eluting the microbial DNA from the microporous silica with an elution buffer to release the same, thereby producing the DNA product. Further to this embodiment the method comprises analyzing the DNA product to quantify the DNA or identify the intact cell or a combination thereof.

In one aspect of both embodiments the entrapping step may comprise flowing directionally the microbial suspension through the microporous silicate to capture the intact cells and cell free nucleic acids. In another aspect of both embodiments the releasing step may comprise adding a lysing/binding buffer to the macroporous silicate filter to lyse the captured intact cells and flowing a washing solution at least once through the microporous silicate to remove nuclease treated cell free nucleic acids and contaminants from lysed cells.

In all embodiments and aspects thereof the intact cells may be bacterial cells or fungal cells. Also, the microbial sample may be obtained from a swab taken from plant tissue, human tissue or animal tissue, from a swab taken off a solid surface, from the air, or from a liquid.

Provided herein are methods for isolating nucleic acids from intact cells. A sample comprising intact cells, contaminating dead cells, cell debris and biofilm is obtained. The intact cells are separated from the rest of the sample through two fractions and the DNA is isolated by disrupting the intact cells. The relative abundance of the intact cells in the sample also may be determined. Generally, the sample comprising the cells described above may be obtained from air, or in a liquid such as water or a buffered solution, or from a swab taken off a solid surface including, but not limited to stainless steel, a glass surface, a plastic surface, a surface of a plant matter or a surface of a skin or a surface of a nasal cavity. The nucleic acids isolated from the cells may be DNA or RNA More particularly, the sample is centrifuged to pellet a first fraction comprising the intact cells and the contaminating dead cells. The first fraction is suspended in a buffered solution and a second separation is performed to obtain a second fraction comprising intact cells. Nucleic acids are isolated by disrupting the intact cells from the second fraction.

When the sample is in large volumes, the method comprises capturing by filtration and suspending in a smaller volume of isotonic water or a buffered solution prior to the first separation. Any type of membrane filter having a pore size from about 0.001 to about 10 μm is used. The filter is made from any material, including, but not limited to polycarbonate membrane, a cellulose nitrate membrane, a cellulose acetate membrane, a polyvinylidene fluoride membrane, a polytetrafluoroethylene membrane, a polyethersulfone membrane, a nylon membrane and a polypropylene membrane. Filtration is accomplished by positive air pressure or by negative air pressure by applying a vacuum. One of ordinary skill in this art would be able to select the appropriate membrane filter for the purposes of suspending the cells in a smaller volume.

The first separation may be performed by filtration which results in cells captured on a membrane filter as the first fraction. The first fraction comprising intact cells and the contaminating dead cells are then suspended in isotonic water or a buffered solution before performing the second separation. Membrane filters having the characteristics described above are used for this purpose. The second separation also may be performed by filtration as described for the first separation.

Alternatively, the first separation may be performed by centrifugation that results in a cell pellet as the first fraction. The centrifugation may be performed at a relative centrifugal force of about 1000×g to about 15,000×g. One of ordinary skill in this art would be able to select the appropriate relative centrifugal force value depending on the cells that are being centrifuged. The second separation also may be performed by centrifugation as described for the first separation.

In the methods any appropriate cell disruption method that breaks the cell wall, cell membrane and/or nuclear membrane is employed. Examples include, chemical disruption using chaotropic agents, detergents and chelating agents and/or the use of a strong base such as NaOH, and physical disruption by homogenization, freeze-thawing, sonication or cavitation.

Also provided herein is an alternative method for isolating nucleic acids from intact cells that utilizes a nuclease. The sample is centrifuged to pellet a first fraction comprising the intact cells and the contaminating dead cells. The first fraction is suspended in a nuclease reaction buffer and incubated with a nuclease to degrade nucleic acids in the contaminating dead cells, cell debris and biofilm to obtain a partially nuclease-degraded sample. A second separation is performed on the nuclease-degraded sample to obtain a second fraction comprising intact cells. Nucleic acids are isolated by disrupting the intact cells as described herein.

Another alternative method for isolating nucleic acids from intact cells is based on the complementary attributes of the physical restriction of cell flow through a silica macroporous silicate filter matrix due to tortuosity and, concurrently, the reversible weak adsorptive binding of the cell surface to the silicate surface area presented by the pore around it via Boom chemistry. The cells suspended in a water phase can be captured and concentrated inside of the macroporous silicate matrix pores. Thus captured, the cells may be processed inside of the same macroporous silicate phase by introduction of fluid solutions, both aqueous and non-aqueous, containing reagents suitable for the purpose of modifying or isolating cellular macromolecules, for example, but not limited to, enzymes to process cellular macromolecules or solutes which can change the way that cellular macromolecules interact with the surfaces of the silicate matrix. With the initial cell capture and concentration steps, then enzyme treatment to degrade extracellular DNA and followed by the induction of the Boom chemistry, this method enables cell capture and concentration, removal of dead cell nucleic acids and the nucleic acid purification from captured cells, all performed on a single macroporous silicate matrix.

Particularly, the cellular complement of a cell suspension is captured and concentrated inside the pore structure of the macroporous silicate matrix under physiological conditions of salt, pH and temperature. This enables the cells to remain intact during capture and concentration. Concurrently, small molecules and small cellular debris of other kinds can be washed though the macroporous silica matrix, thereby generating a cellular preparation enriched in intact cells relative to extracellular debris. The cell suspension of cells and cell free DNA may be obtained from rinsing the surface of a plant tissue or an animal tissue with a suitable buffer, or may be obtained by rinsing with a suitable buffer a swab used previously to swab a plant or an animal tissue, including human tissue, or food or a device, or may be a liquid suspension such as, but not limited to, a water sample.

The macroporous silicate filters may comprise fiberglass, glass frit or packed glass beads. A representative silicate matrix may comprise pure $SiO_2$ glass, a borosilicate glass or a glass comprising another silicate matrix composition. The matrix pore size may be about 10 μm to about 50 μm. The cells or intact cells may be bacterial cells, fungal cells, animal cells, human cells or plant cells. The cells may be obtained from a swab taken from plant tissue, human tissue or animal tissue or from a solid surface, from the air or from a liquid. Representative cell sizes are about 1-2 μM for bacteria, about 2-5 μm for fungi and about 5-20 μm for other eukaryotic cells, such as animal cells and plant cells. In a non-limiting example macroporous silica may have a total matrix volume of about 100 μL and may be loaded in a filter mount positioned at the end of a 1 ml pipette or the end of a 1 ml syringe.

Any nuclease may be used. The nuclease may be an endonuclease or an exonuclease or an endo-exonuclease. The nuclease may be a single-stranded nucleic acid specific nuclease or a double-stranded nucleic acid specific nuclease. Nucleases include, but are not limited to, a micrococcal nuclease, a deoxyribonuclease I, a deoxyribonuclease II, an exonuclease IV, an exonuclease V, an exonuclease VI, a ribonuclease A, a ribonuclease H, a ribonuclease III, a exoribonuclease I or an exoribonuclease II, or a combination thereof. Particularly, the nuclease may be a deoxyribonuclease specific for double-stranded DNA. A non-limiting example is a micrococcal nuclease. The nuclease activity in the incubation mixture and the time of digestion is adjusted to be about 10× that required to digest an equivalent amount of purified DNA in the same buffer. In non-limiting examples, the nuclease may be a DNase 1 or a micrococcal nuclease incubated at 5 units per $10^4$ cells for 10 min at 37° C.

Any of the methods for isolating nucleic acids from intact cells may include a method for measuring the relative abundance of intact cells in the sample. Generally, a total cell count is determined, primer pairs amplify a target nucleotide sequence in the nucleic acids isolated from the intact cells and the amplicons generated are correlated with the number of intact cells in the sample. A comparison of total cell count and intact cell count determines relative abundance of intact cells in the sample. If the nucleic acids are RNAs, a reverse transcription is performed prior to amplification to generate cDNA, which is used as the target nucleotide sequence.

The total cell count in the sample may be determined by manual or automated cell counting methods. Alternatively, a total cell count is obtained by performing at least one amplification using nucleic acids isolated from the total cells as a template and quantitating the plurality of amplicons generated.

Amplification may be performed using any method including, but not limited to, a single PCR reaction, a tandem PCR reaction, qPCR, real-time PCR, a gel based PCR and isothermal amplification. The pair of primers have a nucleotide sequence complementary to the target nucleotide sequence in the isolated nucleic acid. The primers may or may not comprise a fluorescent label. For example, a single amplification is performed before the measuring step, wherein the primers are fluorescently labeled to generate a plurality of fluorescent labeled amplicons. Alternatively, the amplification is by PCR that comprises two amplification steps wherein the first amplification uses non-fluorescent primers to generate a plurality of non-fluorescent amplicons. The non-fluorescent amplicons are used as template for a second amplification that uses fluorescent primers to generate a plurality of fluorescent amplicons wherein the fluorescence signal is proportional to the relative abundance of intact cells in the sample. Any fluorescent label may be used, including, but not limited to SYBR Green, CY5, DYLIGHT™ DY647, ALEXA FLUOR® 647, CY3, DYLIGHT™ DY547, or ALEXA FLUOR® 550.

The following examples are given for the purpose of illustrating various embodiments of the invention and are not meant to limit the present invention in any fashion.

EXAMPLE 1

DNase Treatment: Filtration Method

A filter which had previously entrapped both live microbes and contaminating dead cells, cell debris and biofilm from an air or water suspension is subjected to selective DNase treatment on the surface of the filter. DNA in live microbes are not susceptible to DNase degradation since their cell wall and cell membrane are not damaged. On the other hand, as a direct result of DNase treatment of the filter, DNA in dead cells, cell debris and biofilm will be degraded into smaller fragments and thus liberated in the solution phase. Consequently, the living microbe complement of the original sample will remain on the filter. The filter is then removed and processed for microbial DNA analysis by any standard method including PCR and qPCR.

DNase Treatment: Centrifugation Method

A pellet derived from centrifugation, which had previously contained both live microbes and contaminating dead cells, cell debris and biofilm, is subjected to selective DNase treatment. DNA in intact microbes are not susceptible to DNase degradation since their cell wall and cell membrane are not damaged. On the other hand, as a direct result of DNase treatment of the filter, DNA in dead cells, cell debris and biofilm will be degraded into smaller fragments that would not pellet during centrifugation. Consequently, the intact microbe complement of the original sample will remain in the pellet after the second centrifugation step. The pellet is then removed and processed for microbial DNA analysis by any standard method including PCR and qPCR.

Using the methods claimed in this invention is beneficial since one can perform DNA analysis on released nucleic acids without further purification, The DNase can be selectively inactivated by protease treatment and heat treatment under conditions that does not affect microbial DNA for subsequent DNA testing, thus bypassing a purification step prior to DNA analysis.

EXAMPLE 2

DNase 1 Reactivity of DNA in "Live" E. coli Cells Vs the DNase 1 Reactivity of DNA Released from "Dead" E. coli Cells as Assessed by Centrifugation-Based Collection Coupled to Quantitative Real Time PCR (qPCR)

In order to emulate the physical state of the "Dead Cell" DNA released in a biofilm and related cellular debris so that it may be compared to the Intact "Live Cell" DNA in a viable bacterium, E. coli was used as a model. E. coli was cultured to late log phase in standard growth medium. Upon fluid cell culture, the number of "Live" E. coli cells per unit volume was measured by quantitative bacterial plate culture. To generate a matched "Dead" E. coli cell fraction under controlled conditions, twin aliquots of live E. coli were created (105 intact cells each) but one of the two aliquots was heat treated at 100° C. for 10 minutes, thus generating a "Dead" E. coli fraction with the sample overall chemical composition, including the amount of DNA as the matched "Live" cell fraction.

100 µL of each matched sample was then added to 10 µL of 10× deoxyribonuclease I (DNase 1) reaction buffer (500 mM Tris, 50 mM $CaCl_2$, pH 7.5) to yield a final buffer concentration of 50 mM Tris, 5 mM $CaCl_2$, pH 7.5) and then treated with either 1 µL (2 units), 2 µL (4 units) or 4 µL (8 units) of DNase I for 10 minutes at 37° C. Subsequent to DNase I incubation, 1 µL of EDTA (500 mM stock) was added to inactivate the enzyme, and the suspension was treated with 35 uL of PathogenDx Lysis Buffer (PDx, Inc., Tucson Ariz.) and heating to 95 C, followed by, quenching of the lysate with 5 uL of PathogenDx Neutralization Buffer (PDx, Inc., Tucson Ariz.) to adjust the pH to about 7. Thirty five microliters of PathogenDx Sample Buffer (PDx, Inc., Tucson Ariz.) was added and incubated at 55° C. for 45 minutes to degrade microbial proteins and the remaining DNase. One microliter of the resulting neutralized lysate was then added to 14 µL of a qPCR reaction specific for amplification (Table 1) of a ≈200 base pair segment of the bacterial genome.

The qPCR reaction was quantified with standard SYBR Green detection to yield a quantitation cycle (Ct) value (threshold crossing value) from the resulting "real time" PCR curves (9).

TABLE 1

E. coli qPCR parameters

| Steps | Temperature | Time | Cycles |
|---|---|---|---|
| 1 | 95° C. | 10 minutes | 1 |
| 2 | 95° C. | 30 seconds | 40 |
| 3 | 61° C. | 30 seconds | |
| 4 | 72° C. | 1 minute | |
| 5 | 72° C. | 7 minutes | 1 |
| 6 | 15° C. | ∞ | 1 |

| | |
|---|---|
| SEQ ID NO: 1 | 5'GACTCCTACGGGAGGCWGCAG3' |
| Generic Bacterial 337F Forward Primer (E. coli) | |
| Forward Primer Concentration | 200 nM |

TABLE 1-continued

E. coli qPCR parameters

| Steps | Temperature | Time | Cycles |
|---|---|---|---|
| SEQ ID NO: 2 Generic Bacterial 518R Reverse Primer (E. coli) Reverse Primer Concentration | | 5'GTATTACCGCGGCTGCTGG3' 200 nM | |
| Applied Biosystems PowerUp SYBR Green Master Mix. | | Contains Taq polymerase, SYBR Green and all other master mix components. | |
| qPCR Instrument | | Applied Biosystems QuantStudio 3 Real-Time PCR system | |

Results

It is well known that such Ct values are related to the concentration of >200 base pair long DNA remaining. Thus, this method is suitable to support PCR amplification of the 200 base pair E. coli target region. In general, Ct values are proportional to log to the base 2 ($Log_2$) of the concentration of input DNA suitable to support PCR. In the present case, since the number of E. coli in the DNase1 treated samples is identical to the number of E. coli in the matched untreated sample, any change in Ct value due to DNase I treatment would be a direct measure of the fraction of DNA which had been degraded by DNase I treatment. For instance, if matched untreated vs DNase I-treated cells were analyzed and shown to display Ct's of 21 and 25, respectively, the resulting Ct change (25−21=4) would be indicative of a $2^5$-fold reduction in the amount of DNA having greater than 200 base pairs.

FIG. 1 and Table 2 show representative data for live versus dead cell analysis for E. coli using this method.

TABLE 2

Average qPCR Ct values for Live and Dead E. coli Cells

| DNase (units) | Avg Ct value (live) | Avg Ct value (dead) |
|---|---|---|
| 2 | 20.932 | 24.976 |
| 4 | 20.988 | 26.309 |
| 8 | 20.526 | 25.341 |

There it can be seen that at 2 μL (4 units) and 4 μL (8 units) of added DNase I, Ct values increase by about 5 relative units, indicative of a $2^5$ fold (32-fold) reduction in the amount of DNA in the "Dead" cell fraction relative to that in the "Live" E. coli cells. Therefore, it is concluded that DNase I sensitivity may be used to implement the method of the present invention for distinguishing "Live" E. coli from "Dead" E. coli.

EXAMPLE 3

DNase 1 Reactivity of DNA in "Live" E. coli Cells Vs the DNase 1 Reactivity of DNA Released from "Dead" E. coli Cells as Assessed by Centrifugation-Based Collection Coupled to Trypan Blue Staining and Microscopy and Also to Quantitative Real Time PCR (qPCR)

A 200 μL aliquot of an E. coli suspension ($10^4$ CFU/mL) was dispensed into three tubes and the cells separated by centrifugation using standard procedures. Thus, three tubes each with a cell pellet was obtained.

Treatment of Pellet 1 (Test Sample)

The first pellet was suspended in 20 μL of 1× DNase I reaction buffer (10 mM Tris, 0.5 mM $CaCl_2$, 2.5 mM $MgCl_2$ pH 7.6) and treated with either 1 μL (2 units) or 2 μL (4 units) of DNase I at 37° C. for 10 minutes followed by neutralization by adding 1 uL of 500 mM EDTA.

Subsequently 200 μL of phosphate buffered saline (PBS) was added to the sample. The cells were pelleted by centrifugation and the supernatant kept aside. The DNase I treated cell pellet thus obtained was used for trypan blue exclusion analysis as described below.

Treatment of Pellet 2 (Heat-Killed Sample)

The second pellet was suspended in 20 μL of DNase I reaction buffer followed by heat killing the cells for 10 min at 100° C. This pellet was then treated with either 0 μL (negative control), 1 μL (2 units) or 2 μL (4 units) of DNase I at 37° C. After 10 minutes, 200 μL of phosphate buffered saline (PBS) was added to the sample. The cells were pelleted by centrifugation and the supernatant kept aside. The cell pellet thus obtained was used for trypan blue exclusion analysis or lysed followed by PCR and microarray analysis as described below. The purpose of the negative control having no DNase I added was to determine if heat killing alone would reduce DNA content in the re-formed pellet as assessed by PCR and microarray analysis.

Treatment of Pellet 3 (Control Sample)

The third pellet was suspended in 20 μL of DNase I reaction buffer but not heat killed or treated with the enzyme. After 10 minutes at 37° C., 200 μL of phosphate buffered saline (PBS) was added to the sample. The cells were pelleted by centrifugation and the supernatant kept aside. The cell pellet thus obtained was used for trypan blue exclusion analysis or lysed followed by PCR and microarray analysis as described below.

Trypan Blue Staining

Cell pellets from each treatment described above were treated immediately with trypan blue.

Sample Preparation for qPCR

Cell pellets from each treatment described above were prepared for qPCR as described in Example 2. 1 μL of 500 mM EDTA was added followed by 35 uL of PathogenDx Lysis Buffer Solution and heating to 95 C, followed by quenching of the lysate with 5 uL of PathogenDx Neutralization Buffer Solution to adjust the pH to about 7. 35 uL of PathogenDx Sample Buffer Solution was added and incubated at 550 for 45 minutes to degrade microbial proteins and the remaining DNAse. One microliter of the resulting neutralized lysate was then added to 14 μL of a qPCR reaction specific for amplification of a 200 base pair segment of the E. coli-genome.

qPCR parameters were as in Example 2. The PCR reaction was quantified with standard SYBR Green detection to yield a quantitation cycle (Ct) value (threshold crossing value) from the resulting "real time" PCR curves (9).

TABLE 3

Average Ct and Tm values for Live and Dead E coli Cells

| Sample | Sample description | Ct mean | Average Tm |
|---|---|---|---|
| 1A | Test sample, 2 units DNase I | 23.90 | 84.64 |
| 1B | Test sample, 4 units DNase I | 24.13 | 84.44 |
| 2A | Heat-Killed sample, no DNase I | 21.32 | 85.41 |
| 2B | Heat-Killed sample, 2 units DNase I | 24.64 | 84.44 |
| 2C | Heat-Killed sample, 4 units DNase I | 23.87 | 84.28 |
| 3 | Control sample, no DNase I | 21.31 | 85.31 |
| Superlive | Test sample, supernatant from the test sample which was not heat killed. | 24.92 | 85.06 |
| Superdead | Heat-Killed sample, supernatant from the heat-killed sample. | 28.80 | 84.13 |
| NTC | No template control sample | 32.04 | 85.12 |

Results

Figure 2A:
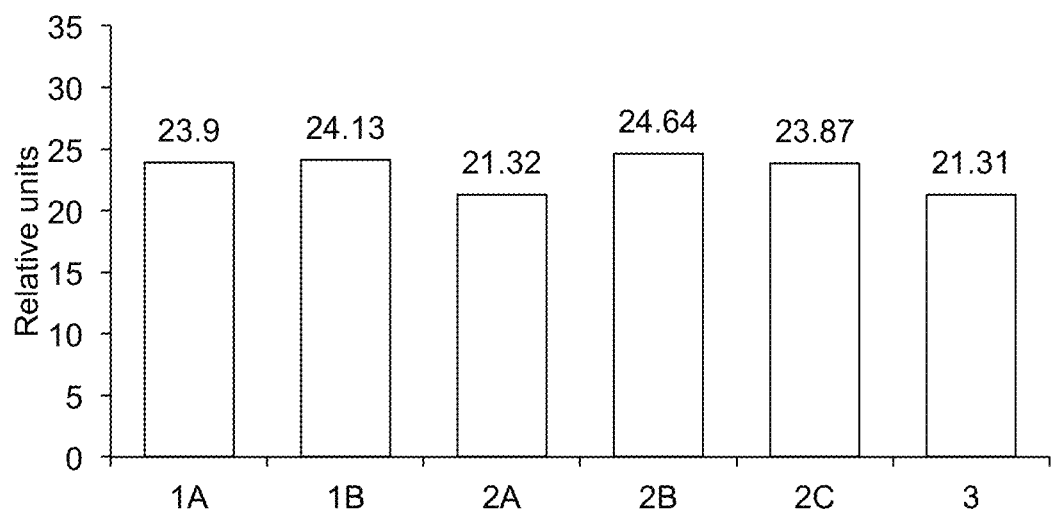
FIGS. 2A-2B shows qPCR analysis for *E. coli* DNA.
Figure 2B:
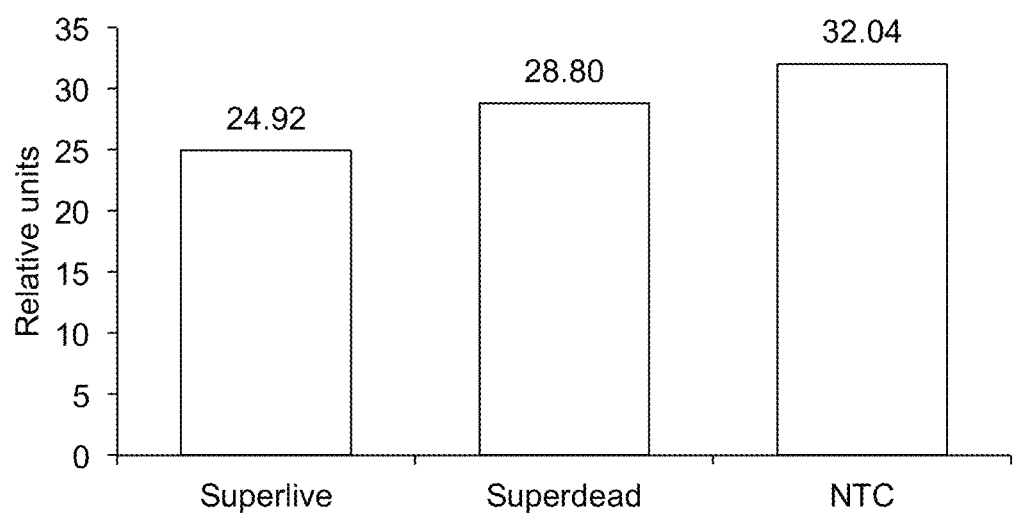
Figure 3:
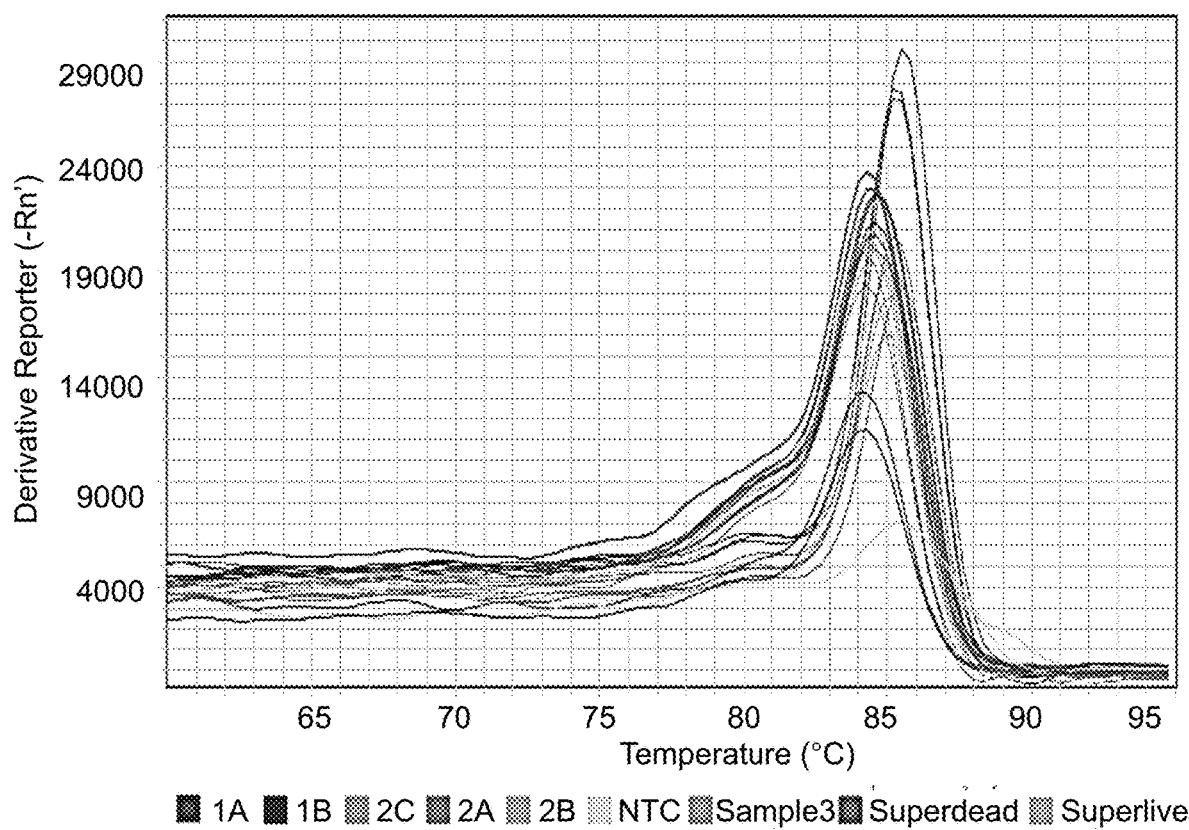
FIG. 3 shows a melt curve plot for DNA in pellet and supernatant samples from live and heat-killed *E. coli* pellets after incubation with or without DNase I.
Figure 4:
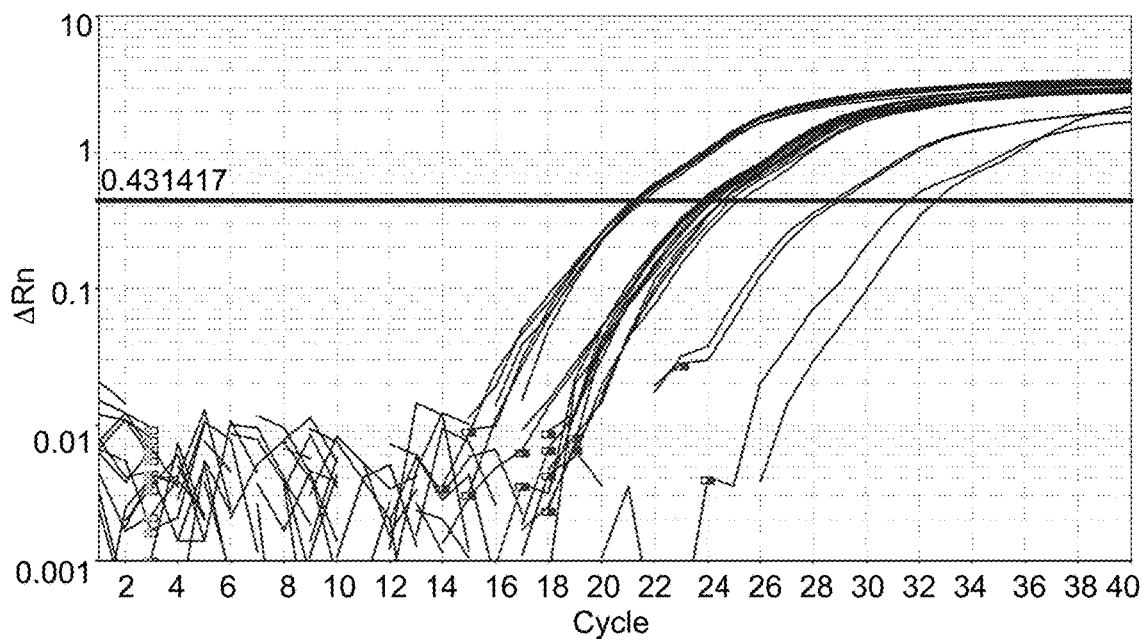
FIG. 4 shows a representative amplification plot.

FIGS. 2A and 2B and Table 3 show the mean Ct values calculated from qPCR performed on the samples treated as discussed above. Average melting temperatures (Tm) obtained from the melt curve (FIG. 3) for this experiment showed a shift in Tm for samples 2A, sample 3, Live and the NTC, which were not treated with DNase I. A representative amplification plot is shown in FIG. 4.

EXAMPLE 4

Micrococcal Nuclease (MN) Reactivity of DNA in "Live" *E. coli* Cells Vs the MN Reactivity of DNA Released from "Dead" *E. coli* Cells as Assessed by Centrifugation-Based Collection Coupled to Microarray Analysis For microbial-testing in the *cannabis* industry, differentiating live from dead pathogenic organisms can make the difference in preventing a health recall. The protocols of the present invention ensure elimination of non-viable cells from pelleted cells, thereby avoiding false positives during DNA amplification.

1. Prepare the micrococcal nuclease MN Enzyme Mix (make fresh each time) in a clean 1.5 mL tube by adding correct volumes of 10× MN Enzyme Buffer, (500 mM Tris, 50 mM $CaCl_2$, pH 7.9) MN Enzyme (New England Biolabs $2 \times 10^{+6}$ units/ml), BSA and Molecular Grade Water based on the number of samples being treated and prepared (Table 4).

TABLE 4

Enzyme Mix for Live Dead Sample Preparation

| Number of Samples | Enzyme Buffer μL | BSA μL | Enzyme μL | Molecular Grade Water μL |
|---|---|---|---|---|
| 1 | 10 | 0.5 | 1 | 88.5 |
| 6 | 60 | 3 | 6 | 531 |
| 12 | 120 | 6 | 12 | 1062 |
| 24 | 240 | 12 | 24 | 2124 |
| 36 | 360 | 18 | 36 | 3186 |

2. Add 100 μL MN Enzyme Mix to microbial samples generated by centrifugation (see below).
3. Heat samples to 37° C. for 15 minutes and remove samples from heat.
4. Add 5 μL 0.5M pH 8.0 EDTA to samples. Vortex for 5 seconds.
5. Centrifuge the samples at 14,000×G for 3 minutes. NOTE: Orient tubes in centrifuge in the same direction to track pellet location
6. Remove supernatant without disturbing the cell pellet.
7. Add 35 μL PathogenDx Lysis Buffer to samples and vortex to dislodge the cell pellet.
8. Heat samples to 95° C. for 10 minutes, remove from heat and perform a quick spin.
9. Add 5 μL of neutralization buffer to samples, for example, PathogenDx Neutralization Buffer. Vortex to ensure proper mix.
10. Add 35 uL of PathogenDx Sample Buffer Mix to each sample tube. Vortex to dislodge the cell pellet.
11. Heat samples at 55° C. for 45 minutes to allow for protease activity.
12. Remove samples from heat and perform a quick spin.
13. Heat samples at 95° C. for 15 minutes.
14. Samples are now ready for PCR. (Vortex and centrifuge briefly prior to use.)

Live/Dead Protocol

The cells were separated into two categories: "Live" and "Dead". The dead cells were lysed by heating for 10 minutes at 100° C. The live and dead cells were then pelleted, the supernatant was aspirated prior to incubation of the resulting pellet sample with micrococcal nuclease (MN) as in Table 4, or buffer control for 15 minutes at 37° C. Enzyme treated cells were pelleted at 15,000×g and the supernatant was decanted prior to cell lysis (PathogenDx Lysis Buffer), neutralization (PathogenDx Neutralization Buffer) then incubation with PathogenDx Sample Buffer Mix to degrade residual cellular protein. Sample lysates were then heated to 95° C. to heat inactivate the PathogenDx Sample Buffer Mix.

Results

Figure 5A:
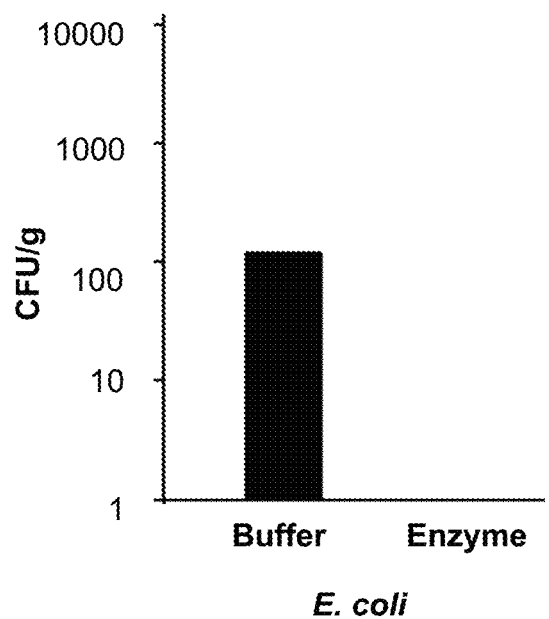
FIGS. 5A-5B show representative QUANT$^X$™ microarray results presented as colony forming units per gram.
Figure 5B:
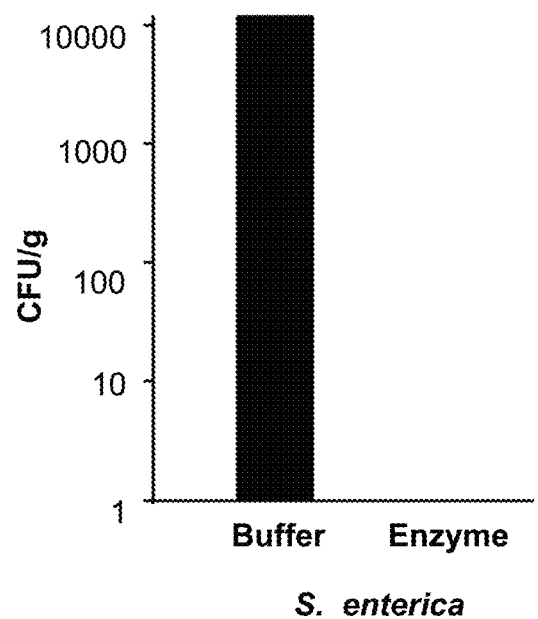

Data obtained from samples processed above via standard deployment of 2-step PCR then hybridization to the QUANTX™ microarray kit (PDx, Inc.) are shown in FIGS. 5A and 5B. Using this protocol, *E. coli* and *S. enterica* samples show an improvement in dead DNA clearance by enzymatic treatment. The results indicate centrifugation alone is not sufficient at clearing the dead DNA. Instead enzymatic degradation of free-floating DNA from dead or compromised cells is necessary as evidenced by the lack of DNA amplification in dead *S. cerevisiae* samples treated with enzyme in the last bar column.

Conclusion

In cases where centrifugation alone is inadequate at eliminating dead DNA in samples (especially fungal cells), the use of extracellular enzymatic DNA degradation using a nuclease (especially micrococcal nuclease) is very effective. Evaluation of the methods demonstrates that enzyme is efficient at eliminating residual free-floating DNA and non-viable cells from solution. The addition of this optional ~20 minute step prior to sample preparation ensures that only DNA intact cells are being amplified.

EXAMPLE 5

Use of Micrococcal Nuclease for Assessment of "Live" Versus "Dead" Microbes as Assessed by qPCR To determine the effect of nuclease digestion on live versus dead cell analysis, a fungal (*Aspergillus niger*) and bacterial (*E. coli* and *S. enterica*) sample were used as models with the endo-exonuclease, micrococcal nuclease MN. The samples were cultured as described in Example 2. To generate a matched "Dead" sample under controlled conditions, twin aliquots of the Live fungal and bacterial samples were created but one of the two aliquots was heat treated at 100° C., thus generating a "Dead" sample having overall chemical composition, including DNA content as in the matched "Live" cell fraction. The "live" and "dead"

samples were pelleted at 15,000×g, and each sample treated with micrococcal nuclease enzyme (as in Example 4) in MN buffer or with micrococcal nuclease buffer alone (no enzyme). After incubation, 1 µL of EDTA (500 mM stock) was added to inactivate the enzyme, followed by lysis of the micrococcal nuclease treated product with PathogenDx Lysis Buffer to release all DNA remaining, followed by, quenching of the lysate with PathogenDx Neutralization Buffer, followed by enzyme treatment in PathogenDx Sample Buffer to degrade residual protein (see Example 4). One microliter of the resulting neutralized lysate was then added to 14 µL of a qPCR reaction specific for amplification of bacterial (*E. coli* and *S. enterica*) and fungal (*A. niger*) specific gene (Table 5). The qPCR reaction was quantified and expressed as "RFU".

Results

Figures 6A, 6B, 6C:
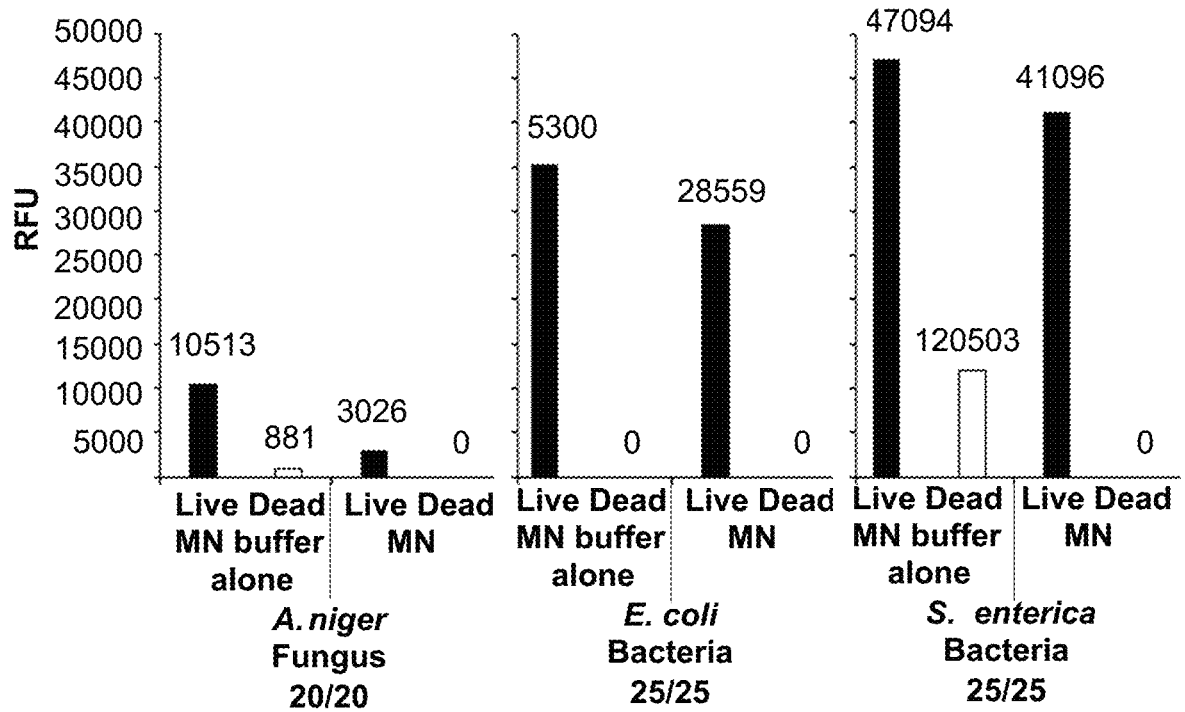
FIGS. 6A-6C show a comparison of qPCR analysis performed in samples processed with and without micrococcal nuclease.

FIGS. 6A-6C show a comparison of the qPCR data for samples processed with micrococcal nuclease enzyme (MN) or with buffer alone ("MN buffer alone"). As shown, inclusion of the micrococcal nuclease results in improved discrimination between "Live" and "Dead" cells, especially for fungal cells.

TABLE 5 qPCR parameters

| Steps | Temperature | Time | Cycles |
|---|---|---|---|
| 1 | 95° C. | 10 minutes | 1 |
| 2 | 95° C. | 30 seconds | 40 |
| 3 | 61° C. | 30 seconds | |
| 4 | 72° C. | 1 minute | |
| 5 | 72° C. | 7 minutes | 1 |
| 6 | 15° C. | ∞ | 1 |
| SEQ ID NO: 1 (*E. coli*) Generic Bacterial 337F Forward Primer Forward Primer Concentration | | 5'GACTCCTACGGGAGGCWGCAG3' 200 nM | |
| SEQ ID NO: 2 (*E. coli*) Generic Bacterial 518R Reverse Primer Reverse Primer Concentration | | 5'GTATTACCGCGGCTGCTGG3' 200 nM | |
| SEQ ID NO: 1 (*S. enterica*) Generic Bacterial 337F Forward Primer Forward Primer Concentration | | 5'GACTCCTACGGGAGGCWGCAG3' 200 nM | |
| SEQ ID NO: 2 (*S. enterica*) Generic Bacterial 518R Reverse Primer Reverse Primer Concentration | | 5'GTATTACCGCGGCTGCTGG3' 200 nM | |
| SEQ ID NO: 3 (*A. niger*) Generic Fungal ITS3 Forward Primer Seq Forward Primer Concentration | | 5'GCATCGATGAAGAACGCAGC3' 200 nM | |
| SEQ ID NO: 4 (*A. niger*) Generic Fungal ITS4 Reverse Primer Seq Reverse Primer Concentration | | 5'TCCTCCGCTTATTGATATGC3' 200 nM | |
| Applied Biosystems PowerUp SYBR Green Master Mix. | | Contains Taq polymerase, SYBR Green and all other master mix components. | |
| qPCR Instrument | | Applied Biosystems QuantStudio 3 Real-Time PCR system | |

EXAMPLE 6

Physical Enrichment and Biochemical Enrichment of Live Vs Dead Cells as Assessed by PCR then Microarray Analysis Materials and Methods

*E. coli* (ATCC 35150) and *S. enterica* (ATCC 700720) were inoculated into Luria-Bertani Broth or a Trypticase Soy Broth, respectively, from a fresh isolation plate and incubated overnight at 29° C. with shaking at 200 rpm. Growth was monitored until an optical density AT 600 nm of 0.4 was reached prior to preparing 10-fold serial dilutions of cells in phosphate buffered saline to a final concentration of $10^4$ or $10^3$ CFU/mL. *A. niger* (ATCC 16888) was grown on Potato Dextrose Agar plates until sporulation occurred after 6-14 days. Spores were collected in molecular grade water and filtered through a 5 micron filter membrane. Spores were counted on a hemocytometer. 10-fold serial dilutions of cells were prepared in molecular grade water to a final concentration of $10^4$ or $10^3$ CFU/mL. *S. cerevisiae* (ATCC 24657) was grown overnight in Yeast Peptone Dextrose broth and plated onto Trypticase Soy Agar plates and incubated at 29° C. with shaking at 200 rpm. For yeast, growth was monitored until an optical density AT 600 nm of 0.5 was reached prior to preparing 10-fold serial dilutions of cells in phosphate buffered saline to a final concentration of $10^4$ or $10^3$ CFU/mL. For all organisms, 1 mL of cells in suspension were aliquoted into 1.5 mL Eppendorf tubes.

To prepare a "Dead Cell" fraction, freshly cultured bacteria or fungi were suspended in PBS then heated to 95° C. for 15 minutes.

Physical Enrichment

Cells (both Live and Dead) were centrifuged at 14,000×g for 3 minutes to pellet cells under conditions where the debris from lysed cells will sediment more slowly than intact cells. This process can be considered "Physical Enrichment" of intact cells.

Biochemical Enrichment

The supernatant from the "Physical Enrichment" step was aspirated away. The resulting pellet was then suspended in 100 µL of 50 mM Tris-HCl, 5 mM $CaCl_2$ supplemented with 100 µg/mL bovine serum albumin and 2,000 gel units of micrococcal nuclease or 100 µL of 10 mM Tris-HCl, 2.5 mM $MgCl_2$, 0.5 mM $CaCl_2$ supplemented with 24 units of DNase 1. Samples underwent incubation for 15 min at 37° C. 5 µL of 0.5M EDTA was then added to the samples to quench the enzyme reaction. Cells were then pelleted a second time at 14,000×g for 3 min and the supernatant was decanted. The resulting pellet was then subjected to Sample Preparation.
Lysis & Sample Preparation The cell pellet from the Biochemical Enrichment step were suspended in 35 uL of PathogenDx Lysis Buffer then lysed via 15 min of heat treatment at 95° C. 5 uL of PathogenDx Neutralization Buffer solution was then added to the suspended cells to neutralize the lysis and then vortexed prior to addition of 25 uL of PathogenDx Sample Buffer Mix as described in Example 4. Samples were incubated at 55° C. for 45 mins. Samples were then heated at 95° C. to heat-inactivate the PathogenDx Sample Buffer (PDx, Inc., Tucson Ariz.).
Two-Step PCR Two different commercial microarray test kits were used (Detect$^{X\text{TM}}$ and Quant$^{X\text{TM}}$). Both were obtained from PathogenDx (PDx, Inc., Tucson Ariz., Product Numbers: DF001, DB001, QF001, QB001). For both tests, the process begins with the Loci Enhancement PCR Reaction, that is then followed by the Labeling PCR Reaction. See manufacturer product insert for details. The Loci Enhancement PCR master mix was prepared according to assay (Detect$^X$ or Quant$^X$) product insert instructions. Briefly, 24 uL was added to 96 well plate. 1 uL of the neutralized lysate (see above) was added to the each well. The 96 well plate was briefly centrifuged prior to placement in an Applied Biosystems thermocycler 3720. In this Example (30 PCR cycles) of the Loci Enhancement PCR program for Detect$^X$ were performed as follows: 95° C. for 4 minutes, 30 cycles of 95° C. for 30 seconds, 55° C. for 30 seconds, 72° C. for 1 minute, and then 72° C. for 7 minutes with final cooling to 15° C. Loci Enhancement PCR program for Quant$^X$ follows the same cycling parameters, but with 15 PCR cycles used instead.

Figure 7A:
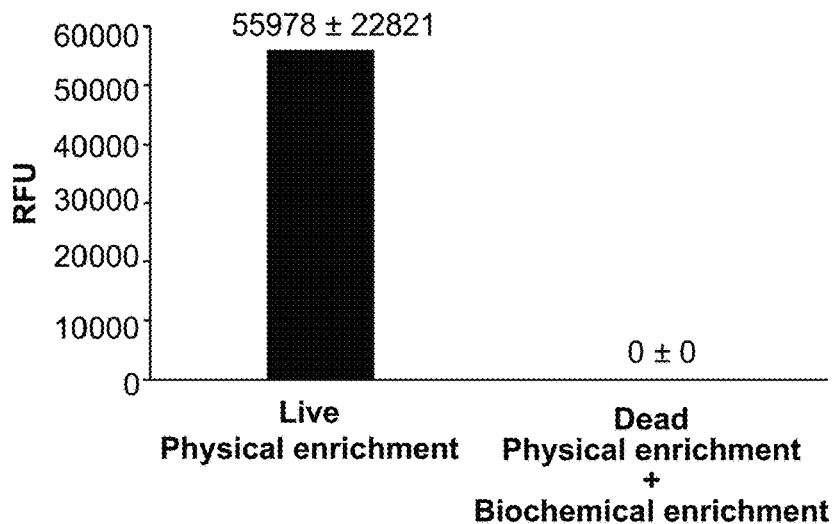
FIGS. 7A-7C show a comparison of microarray results for physical enrichment and biochemical enrichment.
Figure 7B:
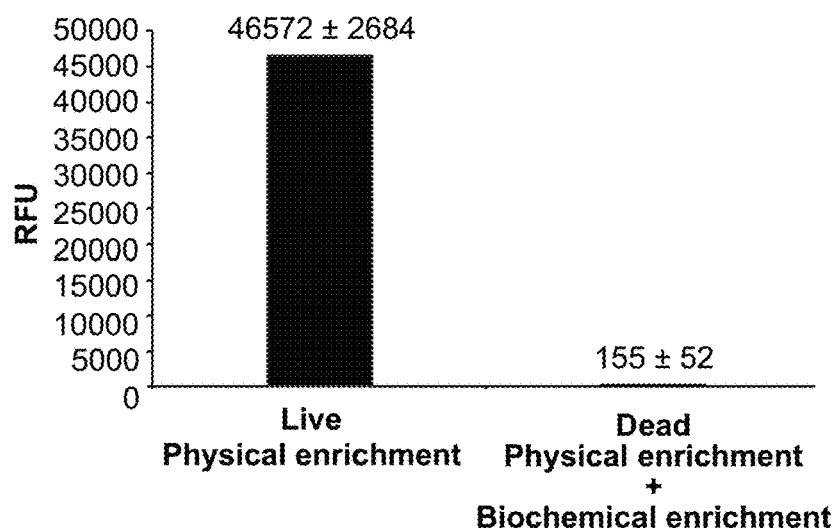
Figure 7C:
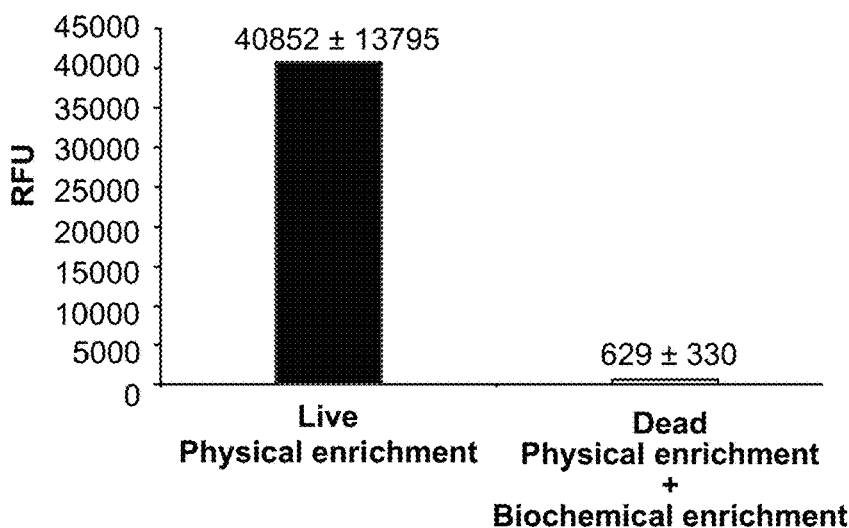

Labeling PCR master mix was prepared according to assay (Detect$^X$ or Quant$^X$) product insert. One microliter of loci enhancement PCR was added to 49 μL of Labeling PCR master-mix in each well of a 96 well plate and placed in an Applied Biosystems thermocycler 3720 for the following cycling parameters for Detect$^X$: 30 cycles of 95° C. for 4 minutes, 30 cycles of 95° C. for 20 seconds, 55° C. for 20 seconds, 72° C. for 30 seconds, and then 72° C. for 7 minutes with final cooling to 15° C. For Quant$^X$ the PCR cycling parameters were exactly as for Detect$^X$ but adjusted to 25 cycles.
Hybridization Detect$^{X\text{TM}}$ or Quant$^{X\text{TM}}$ DNA microarrays (PDx, Inc., Tucson Ariz.) which possess the capacity to analyze by sequence specific hybridization multiple bacteria and fungi, including those of the present example were hydrated with two washes of molecular grade water followed by incubation with Pre-hybridization Buffer (PDx, Inc., Tucson Ariz.). 18 uL of Hybridization Buffer (PDx, Inc., Tucson Ariz.) was added directly to Labeling PCR product in a 96 well PCR plate format. 50 uL of the Hybridization Cocktail was added to microarray wells and allowed to incubate at room temperature for 30 minutes. Wells were aspirated and washed at room temperature with Wash Buffer (PDx, Inc., Tucson Ariz.) a total of three times. The plates were dried by 30 seconds of centrifugation prior to imaging.
Imaging and Analysis The Sensospot® Fluorescence Microarray Analyzer (Sensovation Corp) was used to scan the Detect$^{X\text{TM}}$ and Quant$^{X\text{TM}}$ DNA microarray plates. Image files were uploaded to the cloud and processed via Augury© software, provided with the Detect$^{X\text{TM}}$ and Quant$^{X\text{TM}}$ DNA microarray test kits. Relative fluorescence data (RFU) are presented, which are a direct measure of the fluorescence based hybridization signal obtained from imaging. Data are presented as an average 5 replicates, along with standard error of mean. Students two-tailed t-test was performed to confirm statistical significance (p<0.05).
Results FIGS. 7A-7C demonstrate that biochemical enrichment clears samples of free-floating, non-viable cell DNA. For each of the graphs, the first column represents $10^3$ cells that underwent sample preparation including physical enrichment (PE, centrifugation). The second column represents cells that underwent the kill procedure with biochemical enrichment (BE) prior to the Detect$^{X\text{TM}}$ Sample Prep procedure. Data is displayed as relative fluorescence units (RFU). Mean values are graphed with standard error of mean shown from 5 experiments for each group.

Figure 8A:
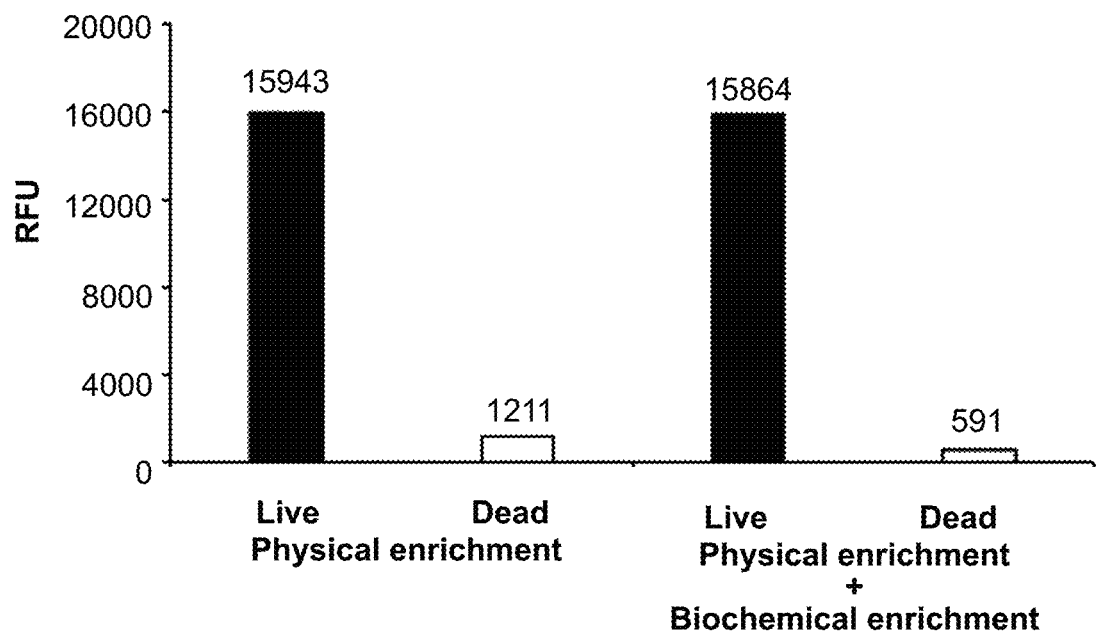
FIGS. 8A-8B show the benefits of biochemical enrichment in clearing free floating DNA.
Figure 8B:
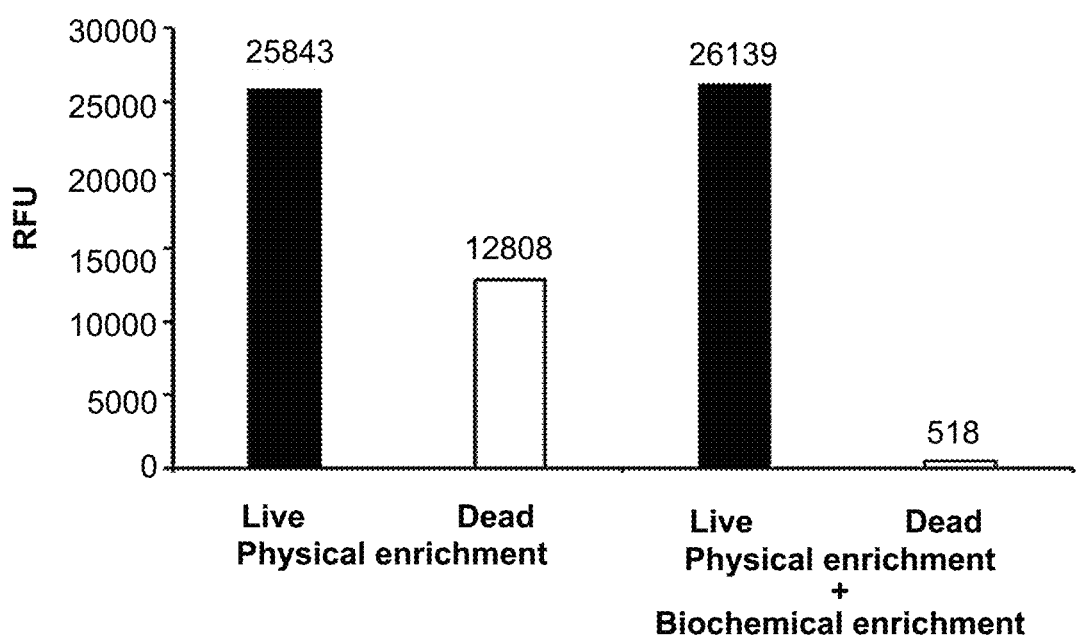

FIGS. 8A and 8B shows the results for *S. enterica* and *S. cerevisiae* and demonstrates that biochemical enrichment is necessary to clear free floating DNA. For each of the graphs, $10^4$ cells/mL underwent the live/dead protocol. Intact cells underwent Quant$^{X\text{TM}}$ sample prep procedures. "Dead" group underwent a kill step prior to biochemical enrichment using micrococcal nuclease and standard Quant$^{X\text{TM}}$ microarray sample prep procedures. Data is displayed as relative fluorescence units.

Figure 9:
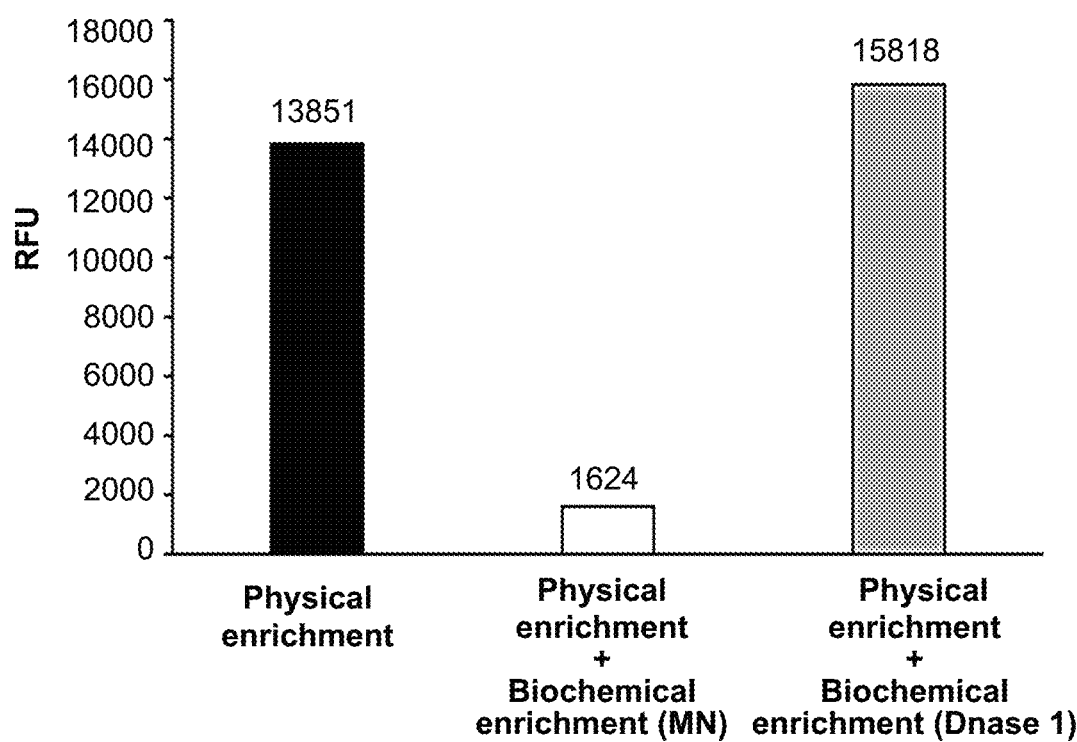
FIG. 9 shows is a comparison of biochemical enrichment in the presence of micrococcal nuclease and DNase I.

FIG. 9 shows that biochemical enrichment with micrococcal nuclease MN is more effective at clearing free-floating DNA than biochemical enrichment with DNase I. $10^4$ cells/mL of *A. niger* underwent the kill procedure. The first column represents the sample prepared via physical enrichment (PE; centrifugation). The second column represents the group of dead cells that underwent physical enrichment via centrifugation (PE) followed by biochemical enrichment (BE) using micrococcal nuclease (MN). The third column represents the same group of dead *A. niger* cells, which underwent physical enrichment followed by biochemical enrichment using DNAse I. Crude sample lysates for all groups were run on the Quant$^{X\text{TM}}$ DNA microarray platform. Representative microarray hybridization data are graphed in relative fluorescence units. Together these data show that micrococcal nuclease is preferable to DNAse 1 for biochemical enrichment.

EXAMPLE 7

Microbial Sterilization with a Fluid Solution of Sterilizing Agents

It is known in the art that live microbes in aerosol suspension or in water suspension or on surfaces may be treated with physical or chemical agents so as to kill the microbes. Examples of such physical sterilization include the application of heat, autoclaving under pressure, UV radiation, or gamma radiation or microwave radiation. Examples of chemical sterilization include treatment with oxidants like $H_2O_2$, perchloric acid and peracetic acid or treatment with agents which disrupt cellular structure, including alcohols like ethanol and isopropanol, detergents like sodium lauryl sulfate and N-lauroylsarcosinate, cationic amphipathic substances like chlorhexidine, organometallic compounds like Povidone-iodine and Merbromin and reactive organic compounds like ethylene oxide vapors. These treatments react both physical and chemical with microbes to disrupt their physical integrity, leading to cell death and the release of microbial nucleic acid. The nucleic acids in the original (intact) living cell structure is resolved from that released during physical or chemical sterilization by the combination of centrifugation and DNase treatment described above.

Sterilization with a Fluid Solution of $H_2O_2$, Peracetic Acid Dissolved into Supercritical Carbon Dioxide It is known in the art that a solution comprising $H_2O_2$ and peracetic acid dissolved in supercritical carbon dioxide ($sCO_2$) at high pressure may be used to sterilize food, agricultural matter, pharmaceutics or delicate surfaces such as medical devices under relatively low temperature conditions. These sterilizing agents do not leave any residue in the materials treated since all these components are volatile at ordinary atmospheric pressure and will therefore spontaneously evaporate-away on completion of the sterilization.

Fungal Sample

*A. niger* is grown in standard Potato dextrose broth (PDB) culture medium to a density of approximately $10^6$ cells/ml. Aliquots of the cell suspension are diluted in PDB to $4 \times 10^4$ cells/ml and 0.25 ml applied to each wafer, which represent any solid surface (e.g. stainless steel, glass, plastic). The fungal aliquots are allowed to air dry at 25° C. for 1 hr to generate a series of air-dried *A. niger* on the surface. Half of these dried fungal surface are treated with $H_2O_2$ and peracetic acid in $sCO_2$ for 15 min at about 5% of $H_2O_2$ and about 5% of peracetic acid.

Upon completion of sterilization, the sterilized wafers and matched, untreated wafers are swabbed with a polyurethane swab capable of holding up to 1 mls of fluid, wetted with 1 ml PBS. The swab containing the *A. niger* on its surface is dispersed by vortexing into 5 ml of PBS. 1 ml of the resulting dispersed *A. niger* suspension is centrifuged and the resulting pellet treated with micrococcal nuclease (MN). The cells are then lysed, and the sample neutralized. PCR and microarray analysis are performed as described for Example 6.

Results

Use of the $H_2O_2$-peracetic acid-$sCO_2$ sterilant kills greater than 95% of the surface associated *A. niger* cells when compared to matched surface samples that are not sterilized. Microarray signals obtained for sterilized samples are reduced by more than 10-fold relative to the samples not sterilized, thus demonstrating that the present invention can distinguish live versus dead *A. niger* cells.

Bacterial Sample

*Staphylococcus aureus* (*S. aureus*) is grown in standard Tryptic soy broth (TSB) culture medium to a density of approximately $10^6$ cells/ml. Aliquots of the cell suspension are diluted in Tryptic soy broth to $4 \times 10^4$ cells/ml and 0.25 ml applied to each wafer, which represent any solid surface (e.g. stainless steel, glass, plastic). The bacterial aliquots are allowed to air dry at 25° C. for 1 hr to generate a series of air-dried *S. aureus* on the surface. Half of these dried bacterial surface are treated with $H_2O_2$ and peracetic acid in $sCO_2$ for 15 min at about 5% of $H_2O_2$ and about 5% of peracetic acid.

Upon completion of sterilization, the sterilized wafers and matched, untreated wafers are swabbed with a polyurethane swab capable of holding up to 1 ml of fluid, wetted with 1 ml PBS. The swab containing the *S. aureus* on its surface is dispersed by vortexing into 5 ml of PBS. 1 ml of the resulting dispersed *S. aureus* suspension is centrifuged, and the resulting pellet treated with micrococcal nuclease (MN). The cells are then lysed, and the sample neutralized. PCR and microarray analysis are performed as described for Example 6.

Results

Use of the $H_2O_2$-peracetic acid-$sCO_2$ sterilant kills greater than 95% of the surface associated *S. aureus* cells when compared to matched surface samples that are not sterilized. Microarray signals obtained for sterilized samples are reduced by more than 10-fold relative to the samples not sterilized, thus demonstrating that the present invention can distinguish live versus dead *S. aureus* cells.

EXAMPLE 8

Sterilization with a Fluid Solution of 4% Chlorhexidine

It is known in the art that a 4% solution of chlorhexidine may be used as a way to sterilize fungal infection on human skin, medical devices and other medically relevant surfaces.

Fungal Sample

*Candida auris* (*C. auris*) is grown in standard PDB culture medium to a density of approximately $10^6$ cells/ml. Aliquots of the cell suspension are diluted in PDB to $4 \times 10^4$ cells/ml and 0.25 ml applied to each wafer, which represent any solid surface (e.g. stainless steel, glass, plastic). The fungal aliquots are allowed to air dry at 25° C. for 1 hr to generate a series of air-dried *A. niger* on the surface. Half of these dried fungal surface are sprayed with 1 ml of 4% chlorhexidine and incubated for 15 min.

Upon completion of sterilization, the sterilized wafers and matched, untreated wafers are swabbed with a polyurethane swab capable of holding up to 1 ml of fluid, wetted with 1 ml PBS. The swab containing the *C. auris* on its surface is dispersed by vortexing into 5 ml of PBS. 1 ml of the resulting dispersed *C. auris* suspension is centrifuged and the resulting pellet treated with micrococcal nuclease. The cells are then lysed, and the sample neutralized. PCR and microarray analysis are performed as described for Example 6.

Results

Use of chlorhexidine kills greater than 95% of the surface associated *C. auris* cells when compared to matched surface samples that are not sterilized. Microarray signals obtained for sterilized samples are reduced by more than 10-fold relative to the samples not sterilized, thus demonstrating that the present invention can distinguish live versus dead *C. auris* cells.

Bacterial Sample

*S. aureus* is grown in standard Tryptic soy broth culture medium to a density of approximately $10^6$ cells/ml. Aliquots of the cell suspension are diluted in Tryptic soy broth to $4 \times 10^4$ cells/ml and 0.25 ml applied to each wafer, which represent any solid surface (e.g. stainless steel, glass, plastic). The bacterial aliquots are allowed to air dry at 25° C. for 1 hr to generate a series of air-dried *S. aureus* on the surface. Half of these dried bacterial surface are sprayed with 1 ml of 4% chlorhexidine and incubated for 15 min.

Upon completion of sterilization, the sterilized wafers and matched, untreated wafers are swabbed with a polyurethane swab capable of holding up to 1 ml of fluid, wetted with 1 ml PBS. The swab containing the *S. aureus* on its surface is dispersed by vortexing into 5 ml of PBS. 1 ml of the resulting dispersed *S. aureus* suspension is centrifuged, and the resulting pellet treated with micrococcal nuclease. The cells are then lysed, and the sample neutralized. PCR and microarray analysis are performed as described for Example 6.

Results

Use of chlorhexidine kills greater than 95% of the surface associated *S. aureus* cells when compared to matched surface samples that are not sterilized. Microarray signals obtained for sterilized samples are reduced by more than 10-fold relative to the samples not sterilized, thus demonstrating that the present invention can distinguish live versus dead *S. aureus* cells.

EXAMPLE 9

Figure 10A:
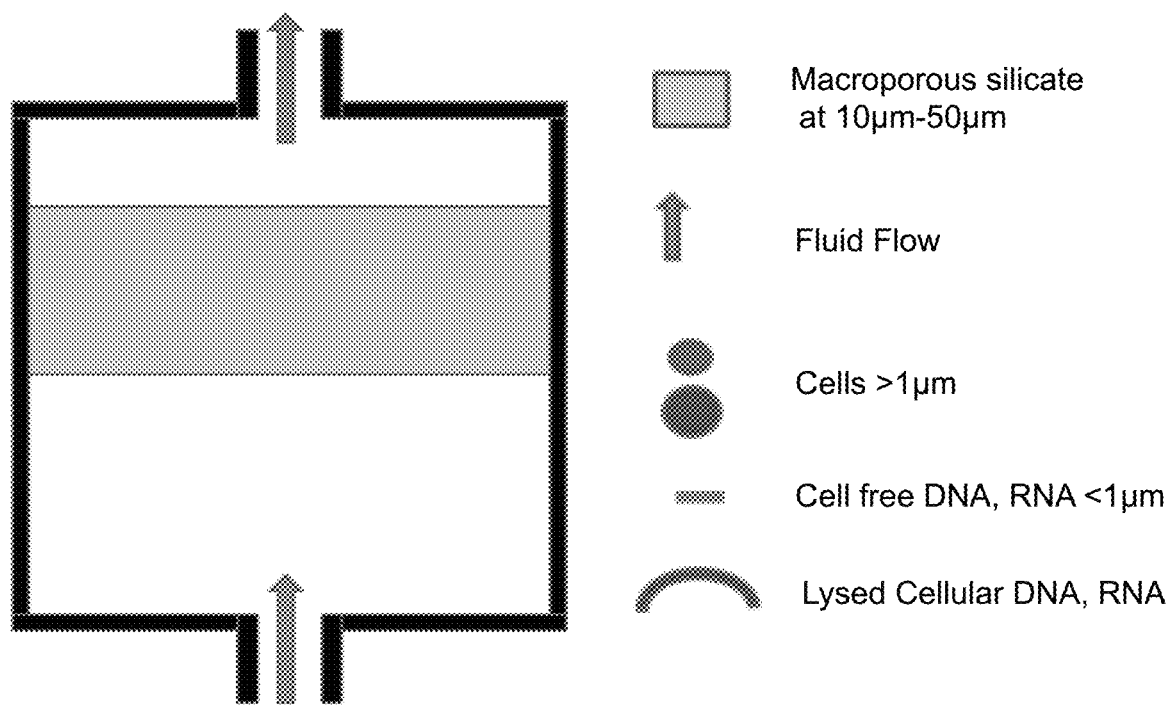
FIGS. 10A-10G are cartoons showing the removal of dead cell nucleic acid within macroporous silicate matrices.
Figure 10B:
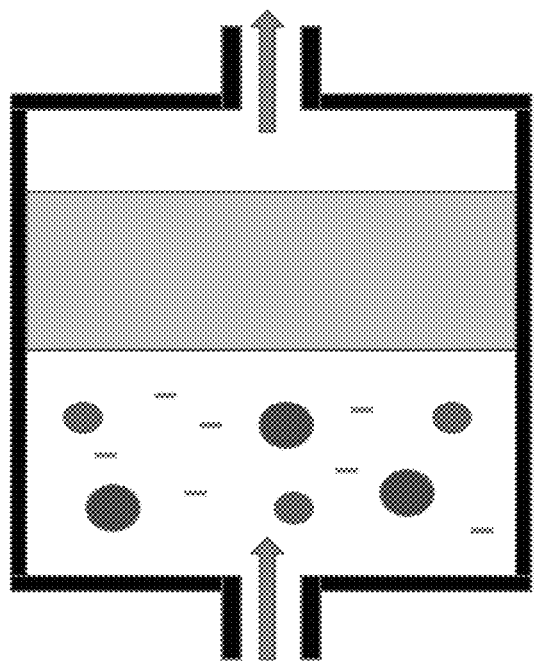
Figure 10C:
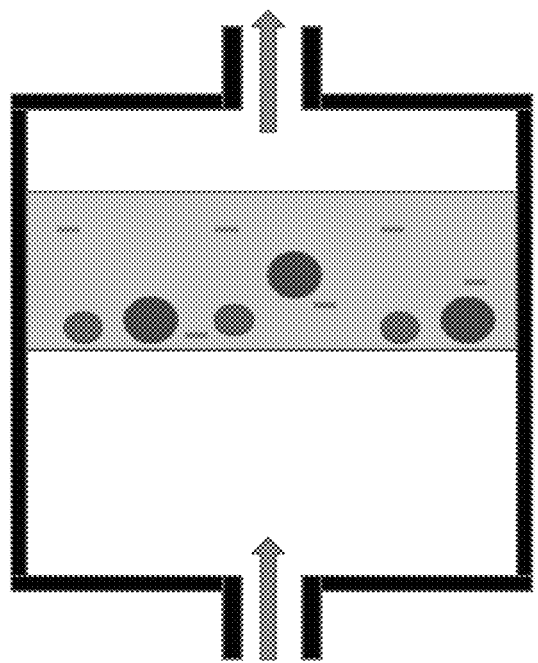
Figure 10D:
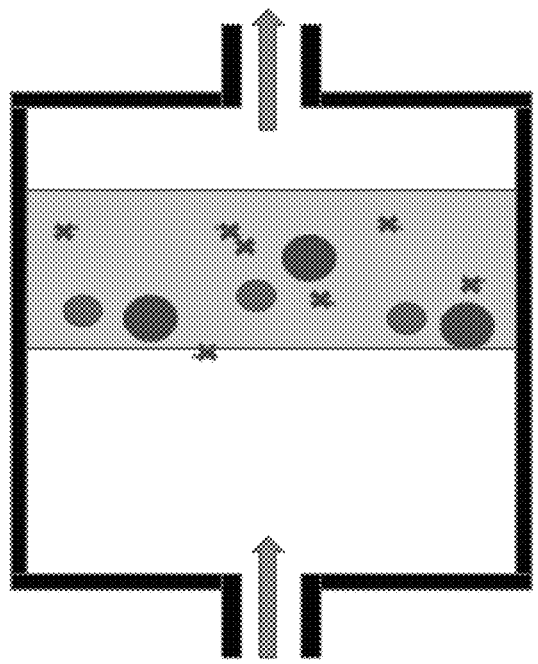

Capture of Cells and Nucleic Acid Purification on a Single Macroporous Silicate Filter General Process FIG. 10A illustrates a macroporous silicate ($SiO_2$) filter disposed in a flow chamber and the direction of flow. The process of cell capture and washing are shown in FIGS. 10B-10C. Upon capture of the cells within the macroporous silicate matrix with pores of 10 μm to 50 μm in size, the cells entrapped within the macroporous silicate phase are treated with a nuclease such as micrococcal nuclease or other nucleases to degrade any extracellular DNA that also became entrapped along with cells in the macroporous silicate matrix. In FIG. 10D that enzyme treatment is used to retain cellular DNA for subsequent nucleic acid based testing, while eliminating the DNA complement of cell free debris such as derived from dead cells and contaminating biofilms.

Figure 10E:
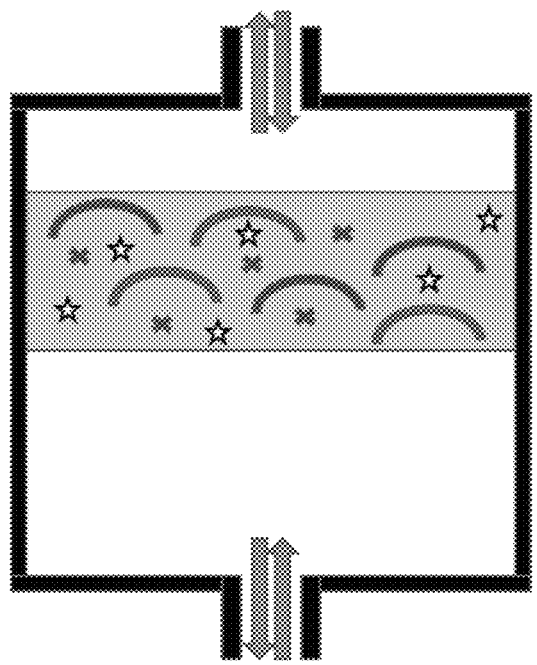

As shown in FIG. 10E, once intact cells had been captured, concentrated, washed and enzyme treated in that way, the silicate matrix (with cells still retained inside) can then be activated by addition of about 4M GuSCN and 25%-50% ethanol. Upon such addition of chaotrope and alcohol (which can be done by applying such a lysis/binding buffer the silicate matrix, such as by simple pipetting, the cells entrapped physically in the macroporous phase then lyse, their DNA complement is dissociated from cellular nucleoprotein and, concurrently, the liberated DNA and RNA chains will bind to the large excess of the silicate surface presented by the macroporous assembly surrounding the sample.

Figure 10F:
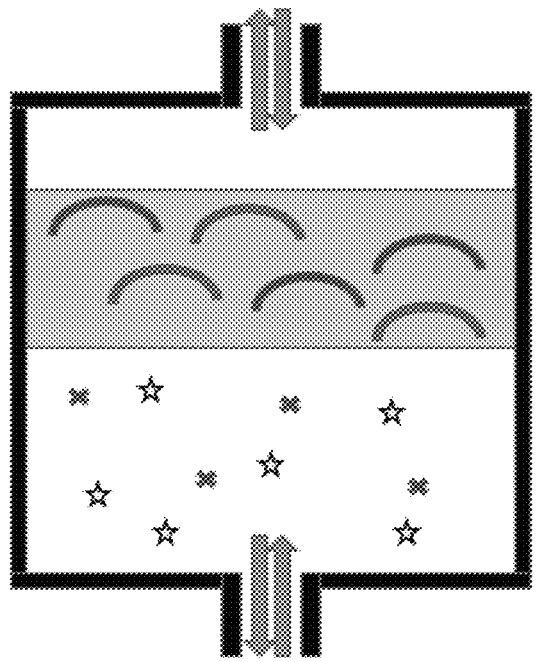
Figure 10G:
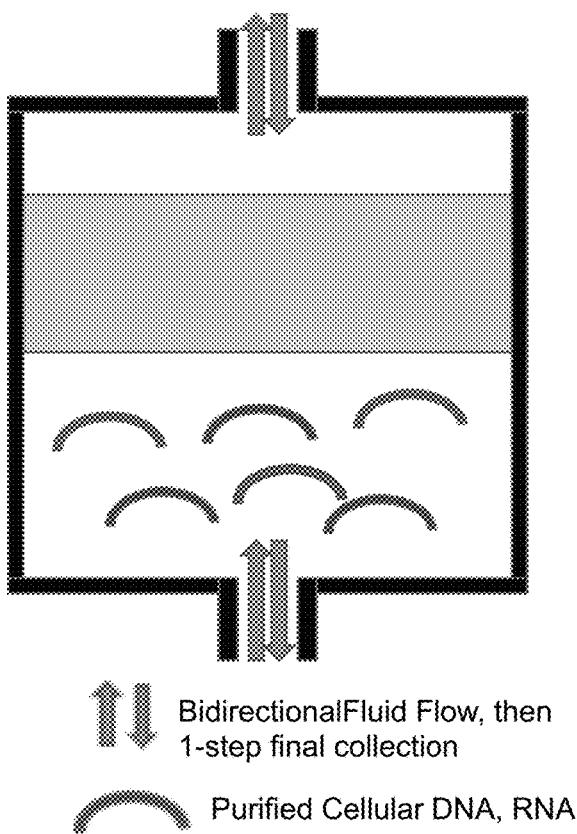

As shown in FIGS. 10F-10G, once the DNA or RNA becomes bound to the surrounding silicate matrix surface, based on well-know Boom chemistry, the nucleic acid can be "washed" by treatment with an alcohol water mixture (typically ethanol/water or Isopropanol water) so as to elute non-nucleic acid contaminants. Once washed the bound DNA or RNA can be eluted from the silicate matrix via treatment with a low salt buffer such as 10 mM Tris/HCl or unbuffered $H_2O$ with pH kept near to or about 7.

Specific Protocol

A single macroporous $SiO_2$ matrix is utilized to capture cells within the matrix, to remove dead cell nucleic acid and to purify nucleic acids from the captured cells via the following steps:

1). Pull about 1 ml of a cellular suspension in a buffer, such as PBS, through the macroporous silicate filter, then gently eject the same 1 ml back to waste. Under these conditions, the cells are trapped physically and by weak adsorptive binding (mediated by hydrogen bonding, van der Waals interaction and electrostatic charge) within the pores of the macroporous silicate filter matrix. The suspended cells may be bacteria, fungi or may be human cells, animal cells, or plant cells or obtained from the same.

2. Pull about 200 μL of micrococcal nuclease solution into the void volume of the macroporous silicate filter and allow the nuclease to react in situ for about 10 min to about 30 min. During the incubation time, the extracellular cell-free DNA or DNA in partially disrupted dead cells in the sample is degraded by the enzyme treatment.

3. Pull 1 ml of [4MGuSCN+25% ethanol] solution, a binding and lysis buffer, into and though the filter void, then eject and repeat the uptake and ejection cycle at least 5× to pass the [4MGuSCN+25% ethanol] solution though the $SiO_2$ filter matrix several times. Such repeat passage induces cell lysis chemically and by shear and also to drive the adsorptive binding of DNA and RNA to the silicate surface. Finally, the [4MGuSCN+25% ethanol] solution is ejected from the macroporous silicate filter and stored as waste whereas the cellular DNA and RNA remain bound to the silicate surfaces of the macroporous filter matrix.

4. Pull 1 ml of an isotonic wash buffer, such as PBS or SSC, plus 75% ethanol into and though the filter void. Eject and repeat the uptake and ejection cycle at least 5× to effect DNA and RNA washing. Eject the wash solution from the filter and store as waste where the DNA and RNA remain bound to the silicate surface of the macroporous filter matrix.

5. Pipette air through the filter void >5× to evaporate the alcohol from the wash solution.

6. Pull 0.1 ml of an elution buffer, such as 10 mM TrisHCl or $H_2O$, into the macroporous filter void. Eject and repeat the uptake and ejection cycle at least 5× to effect DNA and RNA washing. Eject the 0.1 ml of product into a tube or plate for nucleic acid testing.

The following references are cited herein.
1. Donlan, R. M. and Costerton, J. W. Clin. Microbiol. Rev. 15:167-193, 2002.
2. Moscoso et al., J. Bacteriol. 188:7785-7795, 2006.
3. Steinberger and Holden, Appl. Environ. Microbiol. 71:5404-5410, 2005.
4. Okay O., J Polym Sci B Polym Phys. 49:551-556, 2011.
5. Tetz et al., Anti-microbial agents and chemotherapy. 53:1204-1209, 2009.
6. Nocker, A. and Camper, A. K., FEMS Microbiol. Lett. 291:137, 2009.
7. Nocker et al., J. Microbiol. Methods 67,310-320, 2006.
8. Alvarez et al., AMB Express. 3(1):1, 2013.
9. Kralik, P. and Ricchi, M., Frontiers in Microbiology Vol. B, Article 8, pages 1-8, 2017.
10. White et al., In PCR Protocols: A Guide to Methods and Applications, (1990) pages 315-322. Edited: Innis, M. A., Gelfand, D. H., Sninsky, J. J., and White T. J.

What is claimed is:

1. A method for isolating nucleic acids from intact cells, comprising the steps of:
   obtaining a sample comprising intact cells and cell free nucleic acids;
   capturing the intact cells and the cell free nucleic acids within a macroporous silicate matrix with pores of 10 μm to 50 μm in size;
   degrading in situ the captured cell free nucleic acids with a micrococcal nuclease;
   releasing cellular nucleic acids from the captured intact cells; and
   eluting the cellular nucleic acids from the macroporous silicate matrix with an elution buffer to produce an isolated nucleic acid product.

2. The method of claim 1, wherein the capturing step comprises:
   suspending the intact cells and the cell free nucleic acids in a suspension buffer to form a cellular suspension;
   flowing directionally the cellular suspension through the macroporous silicate matrix; and
   entrapping the intact cells and the cell free nucleic acids within macroporous silicate matrix pores to concentrate the same therewithin.

3. The method of claim 2, wherein the releasing step comprises:
   flowing a lysis/binding solution at least once through the macroporous silicate matrix to lyse the intact cells to release cellular nucleic acids, said released cellular nucleic acids binding to the macroporous silicate matrix; and
   flowing a washing solution at least once through the macroporous silicate matrix to remove nuclease treated cell free nucleic acids and contaminants from lysed cells.

4. The method of claim 3, wherein the macroporous silicate matrix comprises a glass made of silicon oxide alone or in combination with boron oxide or aluminum oxide.

5. The method of claim 1, wherein the cellular nucleic acids are DNA or RNA or a combination thereof.

6. The method of claim 1, wherein the intact cells are bacterial cells, fungal cells, animal cells, or plant cells.

7. The method of claim 1, wherein the sample is obtained from a swab taken from plant tissue, human tissue or animal tissue, from a swab taken off a solid surface, from the air, or from a liquid.

8. A method for isolating nucleic acids from intact cells, comprising the steps of:
   obtaining a sample comprising intact cells and cell free nucleic acids;
   suspending the sample in a suspension buffer to form a cellular suspension;
   flowing directionally the cellular suspension through a macroporous silicate matrix with pores size of 10 μm to 50 μm in size to capture the intact cells and cell free nucleic acids within pores therein;
   degrading in situ within the macroporous silicate matrix the cell free nucleic acids with a micrococcal nuclease;
   adding a lysing/binding buffer to the macroporous silicate matrix to lyse the captured intact cells to release cellular nucleic acids therefrom, said cellular nucleic acids binding to the macroporous silicate matrix; and adding an elution buffer to the macroporous silicate matrix to elute the cellular nucleic acids therefrom to produce an isolated nucleic acid product.

9. The method of claim 8, wherein prior to adding an elution buffer the method comprises flowing a washing solution at least once through the macroporous silicate matrix to remove nuclease treated cell free nucleic acids and contaminants from lysed cells.

10. The method of claim 8, wherein the cellular nucleic acids are DNA or RNA or a combination thereof.

11. The method of claim 8, wherein the intact cells are bacterial cells, fungal cells, animal cells, or a plant cells.

12. The method of claim 8, wherein the sample is obtained from a swab taken from plant tissue, human tissue or animal tissue, from a swab taken off a solid surface, from the air, or from a liquid.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Generic bacterial 337F forward primer

<400> SEQUENCE: 1
```

```
gactcctacg ggaggcwgca g                                              21

<210> SEQ ID NO 2
<211> LENGTH: 19
<212> TYPE: DNA
<213> ORGANISM: Artificial Sequence
<220> FEATURE:
<223> OTHER INFORMATION: Generic bacterial 518R reverse primer

<400> SEQUENCE: 2
gtattaccgc ggctgctgg                                                 19

<210> SEQ ID NO 3
<211> LENGTH: 20
<212> TYPE: DNA
<213> ORGANISM: Artificial Sequence
<220> FEATURE:
<223> OTHER INFORMATION: Generic forward primer for amplification of the
      ITS3 locus in fungi

<400> SEQUENCE: 3
gcatcgatga agaacgcagc                                                20

<210> SEQ ID NO 4
<211> LENGTH: 20
<212> TYPE: DNA
<213> ORGANISM: Artificial Sequence
<220> FEATURE:
<223> OTHER INFORMATION: Generic reverse primer for amplification of the
      ITS4 locus in fungi

<400> SEQUENCE: 4
tcctccgctt attgatatgc                                                20
```